United States Patent
Halperin et al.

(10) Patent No.: US 10,786,211 B2
(45) Date of Patent: Sep. 29, 2020

(54) MONITORING, PREDICTING AND TREATING CLINICAL EPISODES

(71) Applicant: EARLYSENSE LTD., Ramat Gan (IL)

(72) Inventors: Avner Halperin, Ramat Gan (IL); Guy Meger, Haifa (IL)

(73) Assignee: EARLYSENSE LTD., Ramat Gan (IL)

( * ) Notice: Subject to any disclaimer, the term of this patent is extended or adjusted under 35 U.S.C. 154(b) by 0 days.

(21) Appl. No.: 16/276,880

(22) Filed: Feb. 15, 2019

(65) Prior Publication Data

US 2019/0320987 A1 Oct. 24, 2019

Related U.S. Application Data

(63) Continuation of application No. 14/631,978, filed on Feb. 26, 2015, now Pat. No. 10,238,351, which is a
(Continued)

(51) Int. Cl.
| | |
|---|---|
| *G08B 23/00* | (2006.01) |
| *A61B 5/00* | (2006.01) |
| *A61B 5/0205* | (2006.01) |
| *A61B 5/11* | (2006.01) |
| *G08B 21/02* | (2006.01) |

(Continued)

(52) U.S. Cl.
CPC .............. *A61B 5/746* (2013.01); *A61B 5/002* (2013.01); *A61B 5/02055* (2013.01); *A61B 5/11* (2013.01); *A61B 5/6891* (2013.01); *A61B 5/6892* (2013.01); *A61B 5/7282* (2013.01); *G08B 21/0211* (2013.01); *G08B 21/0461* (2013.01);
(Continued)

(58) Field of Classification Search
CPC ..................................................... A61B 5/746
USPC ........................................ 340/502, 506, 692
See application file for complete search history.

(56) References Cited

U.S. PATENT DOCUMENTS

| | | |
|---|---|---|
| 5,699,038 A | 12/1997 | Ulrich |
| 7,077,810 B2 | 7/2006 | Lange |

(Continued)

FOREIGN PATENT DOCUMENTS

| | | |
|---|---|---|
| JP | 2004358218 A | 12/2004 |
| WO | 2005/074361 A2 | 8/2005 |

(Continued)

OTHER PUBLICATIONS

Office Action dated Jul. 18, 2019 issued in U.S. Appl. No. 14/726,706. 17 pages.

*Primary Examiner* — Tai T Nguyen
(74) *Attorney, Agent, or Firm* — Roach, Brown, McCarthy & Gruber, P.C.; Kevin D. McCarthy

(57) ABSTRACT

Apparatus and methods are described, including apparatus for use with a plurality of clinicians. The apparatus includes a patient-monitoring system, including a plurality of clinical sensors, configured to detect physiological parameters of respective patients, and to generate respective sensor signals in response thereto. At least one output unit is configured to generate an output to clinicians who are caring for the patients, in response to the sensor signals. A monitoring system (a) analyzes clinician performance in responding to the output of the output unit, and (b) generates an indication of a performance level of the clinicians in response to the analyses. Other applications are also described.

20 Claims, 13 Drawing Sheets

Related U.S. Application Data continuation-in-part of application No. 14/458,399, filed on Aug. 13, 2014, now Pat. No. 8,998,830, which is a continuation-in-part of application No. 13/906,325, filed on May 30, 2013, now Pat. No. 8,882,684, which is a continuation-in-part of application No. 12/991,749, filed as application No. PCT/IL2009/000473 on May 10, 2009, now Pat. No. 8,821,418, said application No. 13/906,325 is a continuation-in-part of application No. 13/389,200, filed as application No. PCT/IL2011/050045 on Dec. 7, 2011, now abandoned, said application No. 13/906,325 is a continuation-in-part of application No. PCT/IL2013/050283, filed on Mar. 24, 2013.

(60) Provisional application No. 61/052,395, filed on May 12, 2008, provisional application No. 61/054,754, filed on May 20, 2008, provisional application No. 61/082,510, filed on Jul. 22, 2008, provisional application No. 61/103,276, filed on Oct. 7, 2008, provisional application No. 61/141,677, filed on Dec. 31, 2008, provisional application No. 61/144,743, filed on Jan. 15, 2009, provisional application No. 61/420,402, filed on Dec. 7, 2010, provisional application No. 61/439,971, filed on Feb. 7, 2011, provisional application No. 61/561,962, filed on Nov. 21, 2011, provisional application No. 61/618,792, filed on Apr. 1, 2012, provisional application No. 61/696,326, filed on Sep. 4, 2012, provisional application No. 61/698,736, filed on Sep. 10, 2012, provisional application No. 61/722,810, filed on Nov. 6, 2012, provisional application No. 61/725,513, filed on Nov. 13, 2012, provisional application No. 61/739,033, filed on Dec. 19, 2012, provisional application No. 61/748,081, filed on Jan. 1, 2013, provisional application No. 61/756,003, filed on Jan. 24, 2013, provisional application No. 61/757,739, filed on Jan. 29, 2013, provisional application No. 61/764,541, filed on Feb. 14, 2013, provisional application No. 61/772,553, filed on Mar. 5, 2013.

(51) Int. Cl.
*G08B 21/04* (2006.01)
*G08B 25/00* (2006.01)
*G16H 40/63* (2018.01)

(52) U.S. Cl.
CPC ........... *G08B 25/006* (2013.01); *G16H 40/63* (2018.01); *A61B 5/1115* (2013.01)

(56) References Cited

U.S. PATENT DOCUMENTS

| | | | |
|---|---|---|---|
| 7,314,451 B2 | 1/2008 | Halperin | |
| 7,778,851 B2 | 8/2010 | Schoenberg | |
| 8,376,954 B2 | 2/2013 | Lange | |
| 8,403,865 B2 | 3/2013 | Halperin | |
| 8,452,610 B2 * | 5/2013 | Lipner | G06Q 50/22 705/2 |
| 8,491,492 B2 | 7/2013 | Shinar | |
| 8,517,953 B2 | 8/2013 | Lange | |
| 8,585,607 B2 | 11/2013 | Klap | |
| 8,603,010 B2 | 12/2013 | Lange | |
| 8,679,030 B2 | 3/2014 | Shinar | |
| 8,679,034 B2 | 3/2014 | Halperin | |
| 8,731,646 B2 | 5/2014 | Halperin | |
| 8,734,360 B2 | 5/2014 | Klap | |
| 8,821,418 B2 | 9/2014 | Meger | |
| 8,840,564 B2 | 9/2014 | Pinhas | |
| 8,882,684 B2 | 11/2014 | Halperin | |
| 8,942,779 B2 | 1/2015 | Halperin | |
| 8,992,434 B2 | 3/2015 | Halperin | |
| 8,998,830 B2 | 4/2015 | Halperin | |
| 9,026,199 B2 | 5/2015 | Halperin | |
| 2005/0148831 A1* | 7/2005 | Shibata | A61B 5/0002 600/300 |
| 2005/0168341 A1 | 8/2005 | Reeder | |
| 2005/0179536 A1* | 8/2005 | Lederer, IV | G08B 7/06 340/506 |
| 2006/0181424 A1 | 8/2006 | Graves | |
| 2007/0118054 A1 | 5/2007 | Pinhas | |
| 2008/0004499 A1* | 1/2008 | Davis | G06F 19/3418 600/300 |
| 2008/0004904 A1 | 1/2008 | Tran | |
| 2008/0114260 A1 | 5/2008 | Lange | |
| 2008/0275349 A1 | 11/2008 | Halperin | |
| 2010/0001838 A1 | 1/2010 | Miodownik | |
| 2010/0217618 A1 | 8/2010 | Piccirillo | |
| 2012/0132211 A1 | 5/2012 | Halperin | |
| 2012/0253142 A1 | 10/2012 | Meger | |
| 2013/0174345 A1 | 7/2013 | Leu | |
| 2013/0245389 A1 | 9/2013 | Schultz | |
| 2013/0245502 A1 | 9/2013 | Lange | |
| 2013/0267791 A1 | 10/2013 | Halperin | |
| 2014/0005502 A1 | 1/2014 | Klap | |
| 2014/0371635 A1 | 12/2014 | Shinar | |
| 2015/0164433 A1 | 6/2015 | Halperin | |
| 2015/0164438 A1 | 6/2015 | Halperin | |
| 2015/0190087 A1 | 7/2015 | Shinar | |
| 2015/0327792 A1 | 11/2015 | Shinar | |
| 2016/0058428 A1 | 3/2016 | Shinar | |
| 2016/0058429 A1 | 3/2016 | Shinar | |
| 2016/0120466 A1 | 5/2016 | Halperin | |
| 2016/0371449 A1 | 12/2016 | Brouse | |
| 2017/0231545 A1 | 8/2017 | Shinar | |
| 2017/0281017 A1 | 10/2017 | Halperin | |
| 2018/0220897 A1 | 8/2018 | Meger | |
| 2019/0083044 A1 | 3/2019 | Halperin | |
| 2019/0090860 A1 | 3/2019 | Shinar | |
| 2019/0183353 A1 | 6/2019 | Halperin | |
| 2019/0254570 A1 | 8/2019 | Shinar | |

FOREIGN PATENT DOCUMENTS

| | | |
|---|---|---|
| WO | 2006/137067 A2 | 12/2006 |
| WO | 2007/052108 A2 | 5/2007 |
| WO | 2007/081629 A2 | 7/2007 |
| WO | 2008/135985 A1 | 11/2008 |
| WO | 2015/008285 A1 | 1/2015 |
| WO | 2017/138005 A2 | 8/2017 |
| WO | 2019/053719 A1 | 3/2019 |

* cited by examiner

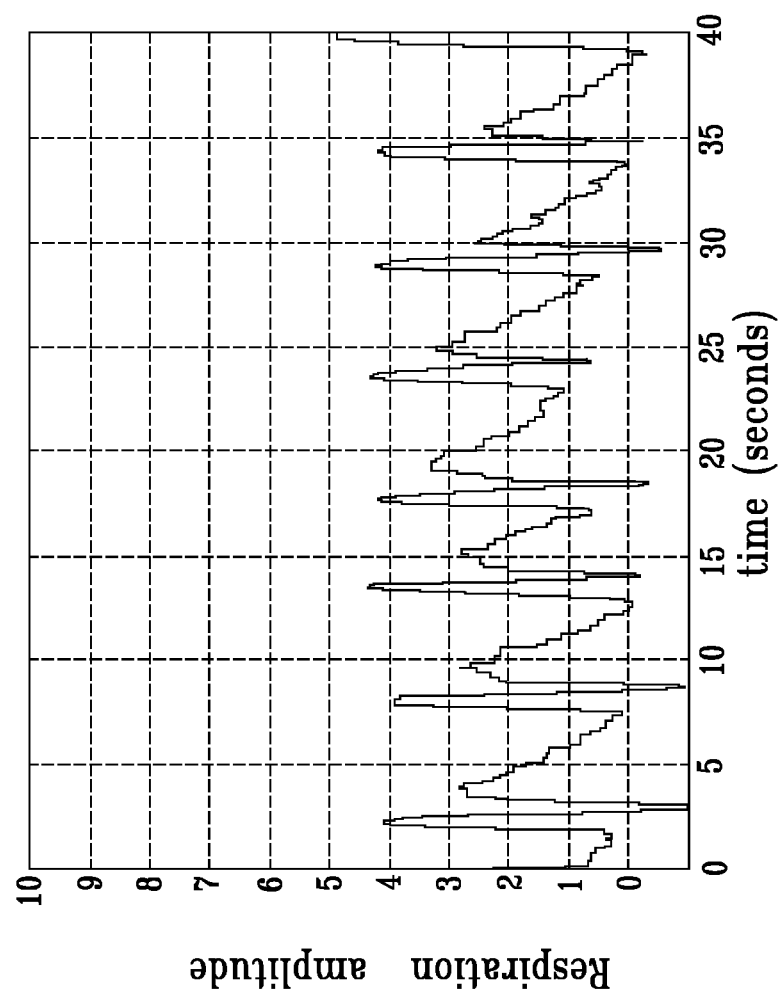

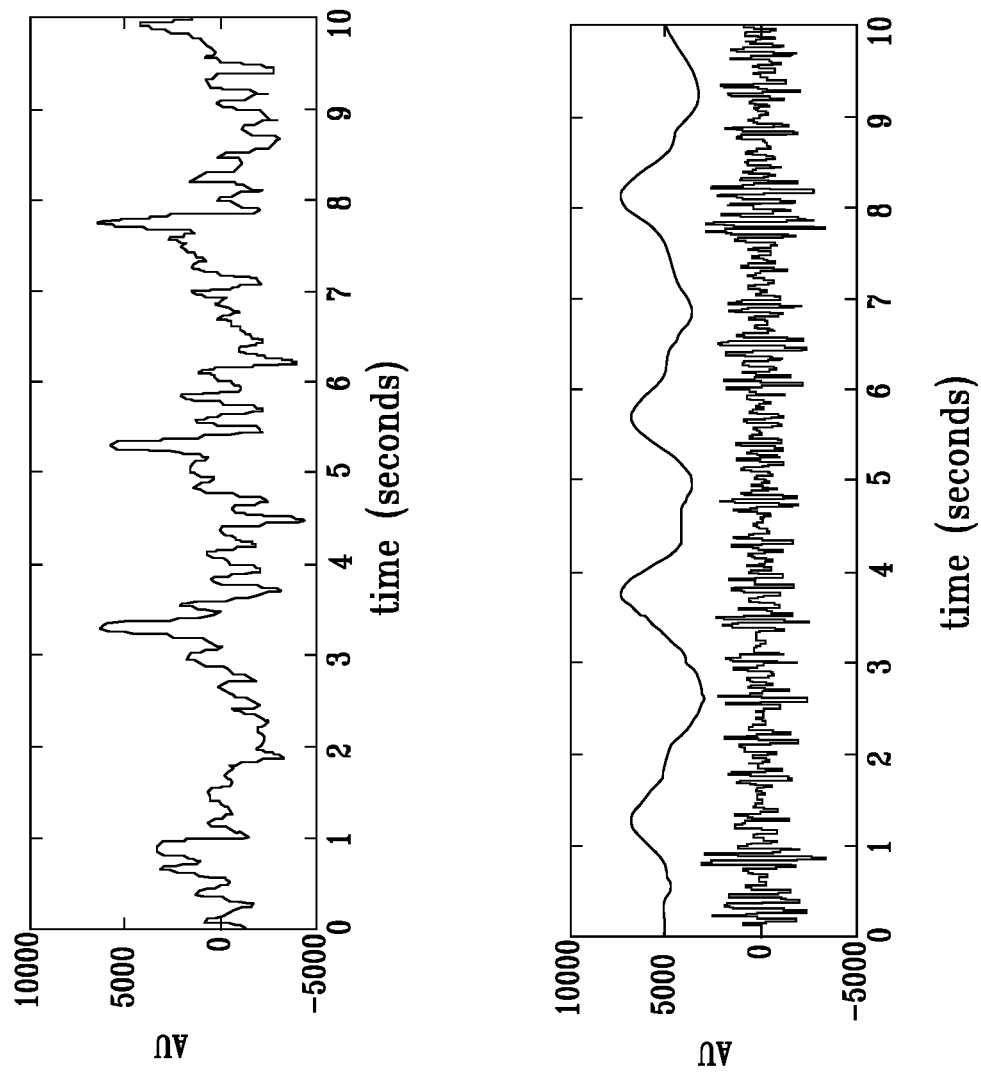

MONITORING, PREDICTING AND TREATING CLINICAL EPISODES

CROSS-REFERENCES TO RELATED APPLICATIONS

The present application is a continuation of U.S. patent application Ser. No. 14/631,978 (issued as U.S. Pat. No. 10,238,351), filed Feb. 26, 2015, which is a continuation-in-part of U.S. patent application Ser. No. 14/458,399 (issued as U.S. Pat. No. 8,998,830), filed Aug. 13, 2014, which is a continuation-in-part of U.S. patent application Ser. No. 13/906,325 (issued as U.S. Pat. No. 8,882,684), filed May 30, 2013, which is a continuation-in-part of:

(i) U.S. patent application Ser. No. 12/991,749, filed Nov. 9, 2010 (issued as U.S. Pat. No. 8,821,418), which is a US national phase of PCT Application No. PCT/IL2009/000473 (published as WO 09/138976), filed May 10, 2009, which claims the benefit of the following US provisional patent applications:
   U.S. Provisional Application 61/052,395, filed May 12, 2008,
   U.S. Provisional Application 61/054,754, filed May 20, 2008,
   U.S. Provisional Application 61/082,510, filed Jul. 22, 2008,
   U.S. Provisional Application 61/103,276, filed Oct. 7, 2008,
   U.S. Provisional Application 61/141,677, filed Dec. 31, 2008, and
   U.S. Provisional Application 61/144,743 filed Jan. 15, 2009;
(ii) U.S. patent application Ser. No. 13/389,200, filed Jun. 13, 2012 (published as US 2012/0253142 and now abandoned), which is a US national phase of International Application PCT/IL2011/050045 (published as WO 12/077113), filed Dec. 7, 2011, which claims the benefit of the following US provisional patent applications:
   U.S. Provisional Application 61/420,402, filed Dec. 7, 2010;
   U.S. Provisional Application 61/439,971, filed Feb. 7, 2011; and
   U.S. Provisional Application 61/561,962, filed Nov. 21, 2011; and
(iii) International Application PCT/IL2013/050283 (published as WO 13/150,523), filed Mar. 24, 2013, which claims priority from the following US provisional patent applications:
   U.S. Provisional Patent Application No. 61/618,792, filed Apr. 1, 2012;
   U.S. Provisional Patent Application No. 61/696,326, filed Sep. 4, 2012;
   U.S. Provisional Patent Application No. 61/698,736, filed Sep. 10, 2012;
   U.S. Provisional Patent Application No. 61/722,810, filed Nov. 6, 2012;
   U.S. Provisional Patent Application No. 61/725,513, filed Nov. 13, 2012;
   U.S. Provisional Patent Application No. 61/739,033, filed Dec. 19, 2012;
   U.S. Provisional Patent Application No. 61/748,081, filed Jan. 1, 2013;
   U.S. Provisional Patent Application No. 61/756,003, filed Jan. 24, 2013;
   U.S. Provisional Patent Application No. 61/757,739, filed Jan. 29, 2013;
   U.S. Provisional Patent Application No. 61/764,541, filed Feb. 14, 2013; and
   U.S. Provisional Patent Application No. 61/772,553, filed Mar. 5, 2013.

All of the above-referenced applications are incorporated herein by reference.

FIELD OF EMBODIMENTS OF THE INVENTION

The present invention relates generally to monitoring patients and predicting and monitoring abnormal physiological conditions and treating those conditions, and specifically to methods and apparatus for predicting and monitoring abnormal physiological conditions by non-contact measurement and analysis of characteristics of physiological and/or physical parameters.

BACKGROUND

Chronic diseases are often expressed by episodic worsening of clinical symptoms. Preventive treatment of chronic diseases reduces the overall dosage of required medication and associated side effects, and lowers mortality and morbidity. Generally, preventive treatment should be initiated or intensified as soon as the earliest clinical symptoms are detected, in order to prevent progression and worsening of the clinical episode and to stop and reverse the pathophysiological process. Therefore, the ability to accurately monitor pre-episodic indicators increases the effectiveness of preventive treatment of chronic diseases.

Many chronic diseases cause systemic changes in vital signs, such as breathing and heartbeat patterns, through a variety of physiological mechanisms. For example, common respiratory disorders, such as asthma, chronic obstructive pulmonary disease (COPD), sleep apnea and cystic fibrosis (CF), are direct modifiers of breathing and/or heartbeat patterns. Other chronic diseases, such as diabetes, epilepsy, and certain heart conditions (e.g., congestive heart failure (CHF)), are also known to modify cardiac and breathing activity. In the case of certain heart conditions, such modifications typically occur because of pathophysiologies related to fluid retention and general cardiovascular insufficiency. Other signs such as coughing and sleep restlessness are also known to be of importance in some clinical situations.

Many chronic diseases induce systemic effects on vital signs. For example, some chronic diseases interfere with normal breathing and cardiac processes during wakefulness and sleep, causing abnormal breathing and heartbeat patterns.

Breathing and heartbeat patterns may be modified via various direct and indirect physiological mechanisms, resulting in abnormal patterns related to the cause of modification. Some respiratory diseases, such as asthma, and some heart conditions, such as CHF, are direct breathing modifiers. Other metabolic abnormalities, such as hypoglycemia and other neurological pathologies affecting autonomic nervous system activity, are indirect breathing modifiers.

SUMMARY OF EMBODIMENTS

Some applications of the present invention provide methods and systems for monitoring patients for the occurrence or recurrence of a physiological event, for example, a chronic illness or ailment. This monitoring assists the patient or healthcare provider in treating the ailment or mitigating the effects of the ailment. Some applications of the present invention provide techniques for monitoring vital and non-vital signs using automated sensors and electronic signal processing, in order to detect and characterize the onset of a physiological event, and, for some applications, to treat the event, such as with therapy or medication.

There is therefore provided, in accordance with some applications of the present invention, apparatus for use with a plurality of clinicians, the apparatus including:
  a patient-monitoring system including:
    a clinical sensor, configured to measure a clinical parameter of a patient, and to generate a clinical-sensor signal in response thereto; and
    a control unit configured:
      in response to the clinical-sensor signal, to determine that an alert event has occurred, and
      in response to having determined that the alert event has occurred, to communicate an alert to a first subset of the plurality of clinicians before communicating the alert to any other clinician,
    the control unit being configured to designate the first subset of the plurality of clinicians in response to respective numbers of alerts that the plurality of clinicians have received within a previous given time period.

In some applications, the control unit is configured to determine whether the alert has been responded to, and, in response to the alert not having been responded to within a given period of time, to communicate the alert to a clinician not in the first subset of the plurality of clinicians.

In some applications, in response to the alert not having been responded to within the given period of time, the control unit is configured to communicate the alert to a more senior clinician than the clinicians in the first subset of clinicians.

In some applications, the control unit is further configured to communicate to the more senior clinician identities of the clinicians in the first subset of the clinicians.

In some applications, the apparatus further includes a location sensing system that includes a plurality of location sensors, the location sensing system being configured to:
  identify respective locations of the plurality of clinicians, and generate a location-sensing-system signal in response thereto, the control unit being configured to designate the first subset of the plurality of clinicians further in response to the location-sensing-system signal.

There is further provided, in accordance with some applications of the present invention, apparatus including:
  a location sensing system that includes a plurality of location sensors, the location sensing system being configured to:
    identify respective locations of a plurality of clinicians, and
    generate a location-sensing-system signal in response thereto; and
  a patient-monitoring system including:
    a clinical sensor, configured to measure a clinical parameter of a patient, and to generate a clinical-sensor signal in response thereto; and
    a control unit configured to:
      in response to the clinical-sensor signal, determine that an alert event has occurred,
      in response to the location-sensing-system signal, designate a first subset of the clinicians,
      in response to having determined that the alert event has occurred, communicate a first alert to the first subset of clinicians, and
      in response to the location-sensing-system signal, communicate a second alert.

In some applications, the control unit is configured to communicate the second alert in response to the location-sensing-system signal indicating that no clinician from the first subset of clinicians is within a given distance of the patient, within a given time period of the first alert.

In some applications, the control unit is configured to communicate the second alert to the first subset of clinicians.

In some applications, the control unit is configured to communicate the second alert to a clinician who is not in the first subset of clinicians.

In some applications, the control unit is configured to communicate the second alert to a more senior clinician than clinicians in the first subset of clinicians.

In some applications, the control unit is further configured to communicate to the more senior clinician identities of the clinicians in the first subset of clinicians.

In some applications, the control unit is configured to communicate the second alert to the first subset of clinicians, in response to the location-sensing-system signal indicating that no clinician from the first subset of clinicians is moving toward the patient within a given time period.

In some applications, in response to determining that no clinician from the first subset of the clinicians is moving toward the patient within the given time period, the control unit is further configured to communicate the second alert to a clinician not in the first subset of clinicians.

In some applications, in response to determining that no clinician from the first subset of the clinicians is moving toward the patient within the given time period, the control unit is configured to communicate the second alert to a more senior clinician than the clinicians in the first subset of clinicians.

In some applications, the control unit is further configured to communicate to the more senior clinician identities of the clinicians in the first subset of clinicians.

There is further provided, in accordance with some applications of the present invention, apparatus for use with a plurality of clinicians, the apparatus including:
  a patient-monitoring system including:
    a clinical sensor, configured to measure a clinical parameter of a patient, and to generate a clinical-sensor signal in response thereto; and
    a control unit configured to:
      in response to the clinical-sensor signal, determine that an alert event has occurred, and
      in response to having determined that the alert event has occurred, (a) compare respective numbers of alerts that the plurality of clinicians have received within a previous given time period, and (b) in response to the comparison, communicate an alert to a subset of the plurality of clinicians before communicating the alert to any other clinician.

In some applications, the control unit is configured such that a likelihood that the control unit will include a given clinician in the subset of clinicians is a decreasing function of the number of alerts received by the given clinician within the previous time period.

In some applications, the control unit is configured to communicate the alert to the subset of the plurality of clinicians in response to each clinician belonging to the subset having received a lower number of alerts during the previous time period than at least one clinician who does not belong to the subset.

In some applications, the control unit is configured to determine whether the alert has been responded to, and, in response to the alert not having been responded to within a given period of time, to communicate the alert to a clinician not in the subset of the plurality of clinicians.

In some applications, in response to the alert not having been responded to within the given period of time, the control unit is configured to communicate the alert to a more senior clinician than the clinicians in the subset of clinicians.

In some applications, the control unit is further configured to communicate to the more senior clinician identities of the clinicians in the subset of the clinicians.

In some applications, the apparatus further includes a location sensing system that includes a plurality of location sensors, the location sensing system being configured to:
identify respective locations of the plurality of clinicians, and
generate a location-sensing-system signal in response thereto,
the control unit being configured to designate the subset of the plurality of clinicians further in response to the location-sensing-system signal.

In some applications, the control unit is configured to designate the subset of the plurality of clinicians in response to the location-sensing-system signal by:
in response to the respective locations of the clinicians, calculating respective estimated times for the clinicians to reach the patient, and
designating the subset of the plurality of clinicians in response to the estimated times. There is further provided, in accordance with some applications of the present invention, apparatus for use with a plurality of patients, the apparatus including:
a plurality of sensors configured to detect physiological parameters of respective patients, and to generate respective sensor signals in response thereto;
at least one output unit configured to generate an output to clinicians who are caring for the patients, in response to the sensor signals; and
a central monitoring system control unit including:
signal-receiving functionality configured to receive the sensor signals;
signal-analysis functionality that is configured to analyze clinician performance in responding to the output of the at least one output unit; and
performance-indication functionality, configured to generate an indication of a performance level of the clinicians in response to the analysis of the signal analysis functionality.

For some applications, the apparatus is for use with a plurality of resting surfaces, respective patients of the plurality of patients resting on respective resting surfaces of the plurality of resting surfaces, and respective sensors of the plurality of sensors are configured to be coupled to respective resting surfaces of the plurality of resting surfaces.

For some applications, the apparatus includes an alert-generation functionality configured to drive the at least one output unit to generate alerts in response to the sensor signals, and the performance-indication functionality is configured to measure the performance level of the clinicians by analyzing a number of alerts generated by the alert-generation functionality over a given period of time.

For some applications, the apparatus includes an alert-generation functionality configured to drive the at least one output unit to generate alerts in response to the sensor signals, and, in measuring the performance level of the clinicians, the performance-indication functionality is configured to account for a level of sensitivity of the alert-generation functionality to respective sensor signals.

For some applications, the performance-indication functionality is configured to generate the indication of the performance level of the clinicians by measuring the performance level of the clinicians with respect to a standard performance level.

For some applications, the performance-indication functionality is configured to measure the performance level of the clinicians with respect to the standard performance level, by measuring the performance level of the clinicians with respect to an average historic performance level over a given time period.

For some applications, the central monitoring system control unit is configured to communicate with at least one similar central monitoring system control unit that is configured to perform monitoring at at least one peer site, and the performance-indication functionality is configured to measure the performance level of the clinicians with respect to the standard performance level, by measuring the performance level of the clinicians with respect to a performance level of clinicians at the at least one peer site, the performance level of the clinicians at the at least one peer site being determined by the at least one similar central monitoring system control unit.

For some applications, the apparatus includes an alert-generation functionality configured to drive the at least one output unit to generate alerts in response to the sensor signals, and the signal analysis functionality is configured to analyze clinician performance by analyzing a response time of the clinicians to the generated alerts.

For some applications, the signal analysis functionality is configured to receive an input from a clinician who is responding to an alert that is indicative of the clinician having responded to the alert, and to analyze clinician performance in response thereto.

For some applications,
the apparatus further includes a location-sensing system configured to identify respective locations of a plurality of clinicians, and to generate a location-sensing-system signal in response thereto, and
the signal analysis functionality is configured to:
receive the location-sensing system signal,
determine that at least one of the clinicians has responded to the alert by analyzing the location-sensing system signal, and analyze clinician performance in response thereto.

For some applications, the signal analysis functionality is configured to:
analyze the sensor signals,
determine that a clinician has responded to an alert by determining that there has been a change in one of the sensor signals that is indicative of a clinician having responded to the alert, and
analyze clinician performance in response thereto.

There is additionally provided, in accordance with some applications of the present invention, apparatus for use with a plurality of patients, the apparatus including:
a plurality of sensors configured to detect physiological parameters of respective patients, and to generate respective sensor signals in response thereto;
at least one output unit;
an alert-generation functionality configured to drive the at least one output unit to generate alerts in response to the plurality of sensor signals; and
a central monitoring system control unit including signal analysis functionality that is configured to:
analyze a rate at which the alerts are generated, in response thereto, determine that a setting of the alert-generation-functionality should be changed, and in response thereto, perform an action selected from the group consisting of:
generating an output that is indicative of a recommended change to the alert-generation functionality setting, and
automatically changing the alert-generation functionality setting.

For some applications, the apparatus is for use with a plurality of resting surfaces, respective patients of the plurality of patients resting on respective resting surfaces of the plurality of resting surfaces, and respective sensors of the plurality of sensors are configured to be coupled to respective resting surfaces of the plurality of resting surfaces.

For some applications, the signal analysis functionality is configured to generate an output that is indicative of the recommended change to the alert-generation functionality setting in response to determining that a setting of the alert-generation-functionality should be changed.

For some applications, the signal analysis functionality is configured to automatically change the alert-generation functionality setting in response to determining that a setting of the alert-generation-functionality should be changed.

For some applications, the signal analysis functionality is configured to determine that the setting of the alert-generation functionality should be changed by determining that a threshold used by the alert-generation functionality should be changed.

For some applications, the signal analysis functionality is configured to determine that the setting of the alert-generation functionality should be changed in a manner that will lower the rate at which the alerts are generated, in response to the rate at which the alerts are generated exceeding a threshold rate.

For some applications, the signal analysis functionality is configured to determine that the setting of the alert-generation functionality should be changed in a manner that will increase the rate at which the alerts are generated, in response to the rate at which the alerts are generated being below a threshold rate.

For some applications, the signal analysis functionality is configured to determine that the setting of the alert-generation-functionality should be changed by determining that a general setting of the alert-generation functionality should be changed in a manner that affects a response of the alert-generation functionality to each one of the plurality of sensor signals.

For some applications, the signal analysis functionality is configured to determine that the general setting of the alert-generation-functionality should be changed, in response to determining an overall alert rate at which alerts are generated based on the sensor signals from all of the plurality of sensors.

There is further provided, in accordance with some applications of the present invention apparatus for use with a plurality of patients, the apparatus including:
a plurality of sensors configured to detect physiological parameters of respective patients, and to generate respective sensor signals in response thereto;
at least one output unit;
an alert-generation functionality configured to drive the at least one output unit to generate alerts in response to the sensor signals; and
a central monitoring system control unit that is configured to automatically change alert settings of each of the plurality of sensors based on time of day.

For some applications, the apparatus is for use with a plurality of resting surfaces, respective patients of the plurality of patients resting on respective resting surfaces of the plurality of resting surfaces, and respective sensors of the plurality of sensors are configured to be coupled to respective resting surfaces of the plurality of resting surfaces.

In some applications, the control unit is configured to calculate the respective estimated times in response to times that were historically required to traverse portions of a building in which the patient is located.

In some applications,
the control unit is further configured to determine a severity of the alert event, and
the control unit is configured to:
if the severity is less than a threshold, communicate the alert to the subset of clinicians before communicating the alert to any other clinician, and
if the severity is not less than the threshold, communicate the alert to a group of the clinicians that is larger than the subset.

There is further provided, in accordance with some applications of the present invention, apparatus for use with a plurality of clinicians, the apparatus including:
a clinical sensor, configured to measure a clinical parameter of a patient, and to generate a clinical-sensor signal in response thereto; and
a control unit configured to:
identify a historical alert-response time for each of the clinicians,
in response to the clinical-sensor signal, determine that an alert event has occurred, and
in response to determining that the alert event has occurred:
identify a subset of the clinicians in response to the historical alert-response times, and
communicate an alert to the identified subset of clinicians before communicating the alert to any other clinician.

In some applications, the control unit is configured to identify the subset of clinicians by identifying a subset of the clinicians whose respective historical alert-response times are less than the historical alert-response time of at least one clinician who is not a member of the subset.

In some applications, the control unit is configured to identify the subset of clinicians by identifying a subset of clinicians whose respective historical alert-response times are greater than the historical alert-response time of at least one clinician who is not a member of the subset.

In some applications, the control unit is further configured to compare a severity of the alert event to a threshold, and the control unit is configured to identify the subset of the clinicians in response to the comparison.

In some applications, the control unit is configured to:
if the severity of the alert event is greater than the threshold, identify the subset of clinicians by identifying a subset of clinicians whose respective historical response times are less than the historical response time of at least one clinician who is not a member of the subset, and
if the severity of the alert event is not greater than the threshold, identify the subset of clinicians by identifying a subset of clinicians whose respective historical response times are greater than the historical response time of at least one clinician who is not a member of the subset.

The present invention will be more fully understood from the following detailed description of embodiments thereof, taken together with the drawings, in which:

BRIEF DESCRIPTION OF THE DRAWINGS

FIG. 8 is a graph showing a respiratory signal measured on a ventilated patient that had to undergo a tracheostomy, in accordance with some applications of the present invention;

FIGS. 9A-B are sets of graphs showing signals of, respectively, a patient undergoing normal breathing, and a patient undergoing shallow breathing, that were measured and derived, in accordance with some applications of the invention;

DETAILED DESCRIPTION OF EMBODIMENTS

Figure 1:
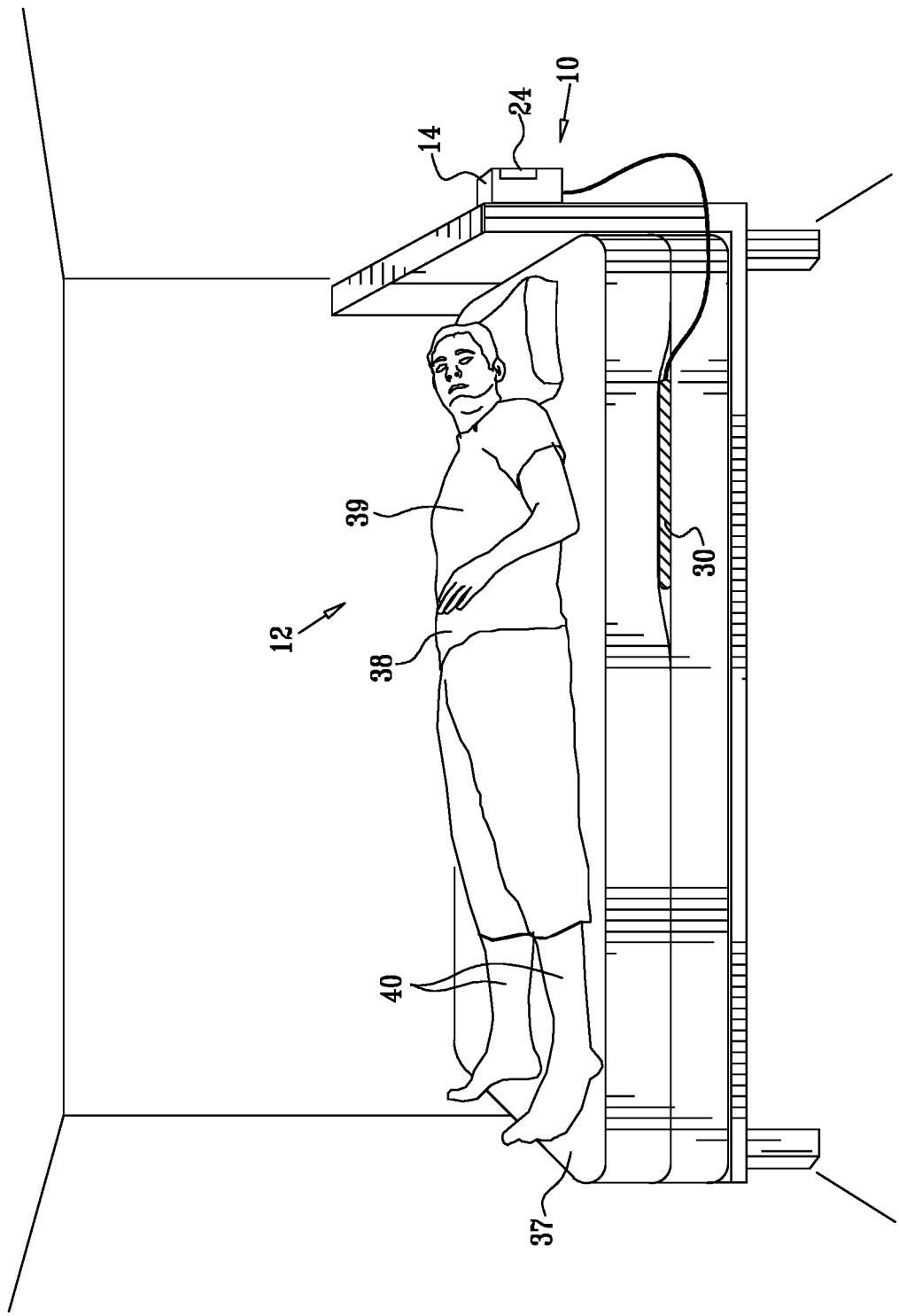
FIG. 1 is a schematic illustration of a system for monitoring a chronic medical condition of a patient, in accordance with some applications of the present invention.

FIG. 1 is a schematic illustration of a system 10 for monitoring a chronic medical condition of a patient 12, in accordance with some applications of the present invention. System 10 typically comprises a motion sensor 30, a control unit 14, and a user interface (U/I) 24. System 10 is generally similar to system 10 described in US 2011/0112442 to Meger (issued as U.S. Pat. No. 8,821,418) and in US 2012/0253142 to Meger (now abandoned), both of which applications are incorporated herein by reference, except for differences described herein. For some applications, user interface 24 is integrated into control unit 14, as shown in the figure, while for other applications, the user interface and the control unit are separate units. Typically, user interface 24 includes a display. For some applications, motion sensor 30 is integrated into control unit 14, in which case user interface 24 is either also integrated into control unit 14 or remote from control unit 14. For some applications, control unit 14 and/or user interface module 24 of system 10 are implemented in a mobile device (such as a cellular phone, a pager, and/or a tablet computer).

In some applications of the present invention, motion sensor 30 is a "non-contact sensor," that is, a sensor that does not contact the body of patient 12 or clothes patient 12 is wearing. In other applications, motion sensor 30 does contact the body of patient 12 or clothes patient 12 is wearing. In the former applications, because motion sensor 30 does not come in contact with patient 12, motion sensor 30 detects motion of patient 12 without discomforting or inconveniencing patient 12. For some applications, motion sensor 30 performs sensing without the knowledge of patient 12, and even, for some applications, without the consent of patient 12. For some applications, motion sensor 30 does not have a direct line of sight with patient 12 or the clothes patient 12 is wearing.

Motion sensor 30 may comprise a ceramic piezoelectric sensor, vibration sensor, pressure sensor, or strain sensor, for example, a strain gauge, configured to be installed under a resting surface 37, and to sense motion of patient 12. The motion of patient 12 sensed by sensor 30, during sleep, for example, may include regular breathing movement, heartbeat-related movement, and other, unrelated body movements, as discussed below, or combinations thereof. For some applications, sensor 30 comprises a standard communication interface (e.g. USB), which enables connection to standard monitoring equipment.

Figure 2:
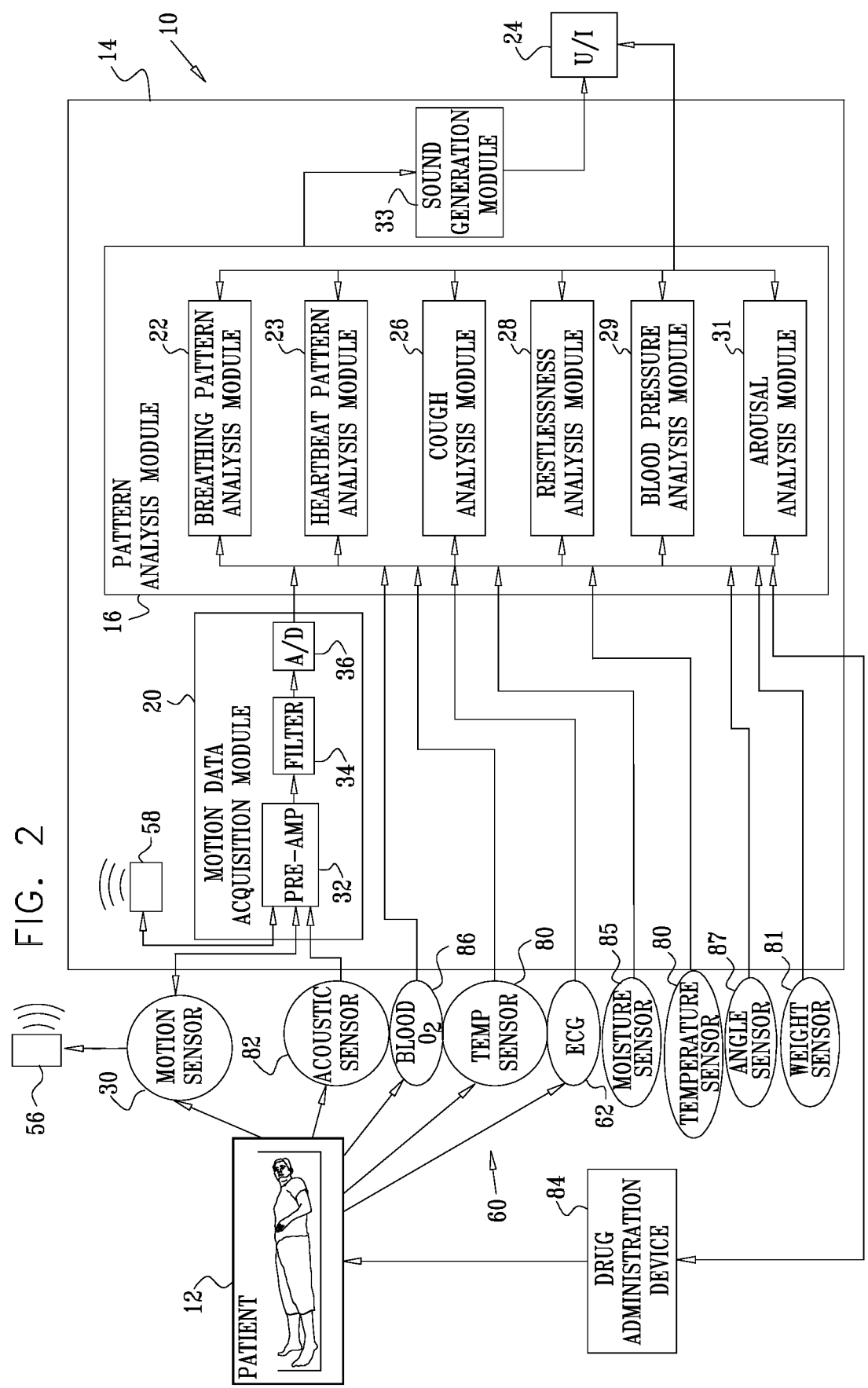
FIG. 2 is a schematic block diagram illustrating components of a control unit of the system of FIG. 1, in accordance with some applications of the present invention.

As shown in FIG. 2 (described hereinbelow), for some applications, in addition to wirelessly-enabled motion sensor 30, control unit 14 is coupled to one or more additional sensors 60 applied to patient 12, such as a blood oxygen monitor 86 (e.g., a pulse oximeter/photoplethysmograph), an ECG monitor 62, weight sensor 81 (e.g. a weight sensor embedded into a bed as manufactured by Stryker Inc. of Kalamazoo, Mich.), a moisture sensor 85, an angle sensor 87, and/or a temperature sensor 80. In accordance with respective applications, one or more of sensors 60 is a contact sensor or a contact-less sensor.

Most of the experimental results presented in the present application were measured using one or more piezoelectric sensors. Nevertheless, the scope of the present invention includes performing measurements with other motion sensors 30, such as other pressure gauges or accelerometers.

Figure 12A:
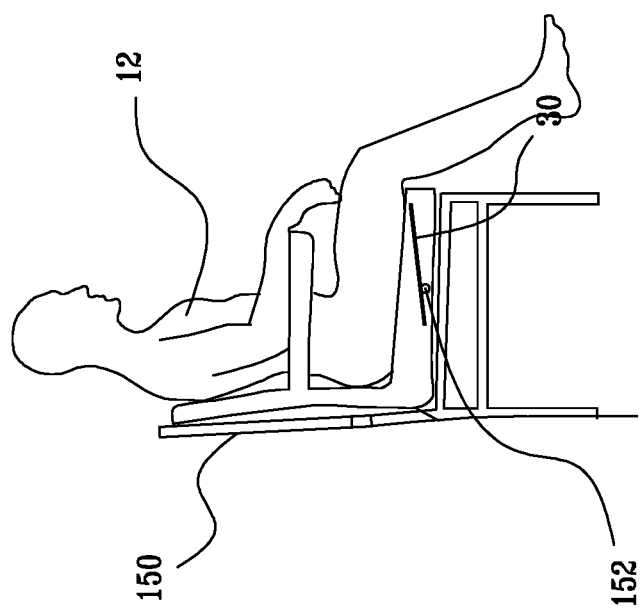
FIGS. 12A-B, are schematic illustrations of a motion sensor coupled to a chair, in accordance with some applications of the present invention.
Figure 12B:
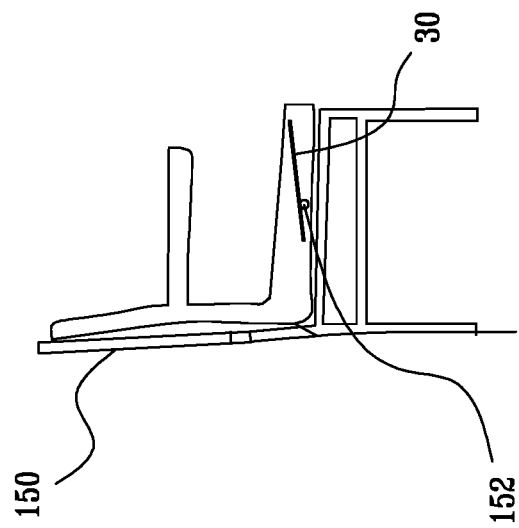

Motion sensor 30 is typically coupled to a resting surface 37 upon which the patient rests. For example, as shown in FIG. 1, motion sensor 30 may be placed under a mattress of a bed, and may sense motion of the patient while the patient is in the bed, and generate a motion sensor signal in response thereto. Alternatively or additionally, as shown in FIGS. 12A-B, motion sensor 30 may be coupled to a chair (e.g., a wheelchair) upon which the patient sits, and may sense motion of the patient while the patient is sitting in the chair, and generate a motion sensor signal in response thereto. For some applications, system 10 includes a first motion sensor which is under the mattress of the patient's bed, and a second motion sensor 30, which is coupled to a chair in the patient's room. The first sensor senses motion of the patient while the patient is in the bed, and the second motion sensor senses motion of the patient while the patient is in the chair. System 10 monitors the patient responsively to both the first and the second sensor signals, as described in further detail hereinbelow. For some applications, a plurality of motion sensors are coupled to a single resting surface, and are used as motion sensor 30. For example, two or more motion sensors that are disposed under the patient's mattress may be used as motion sensor 30. Alternatively, only a single sensor is coupled to a given resting surface.

FIG. 2 is a schematic block diagram illustrating components of control unit 14 in accordance with some applications of the present invention. Control unit 14 typically comprises a motion data acquisition module 20 and a pattern analysis module 16. Pattern analysis module 16 typically comprises one or more of the following modules: a breathing pattern analysis module 22, a heartbeat pattern analysis module 23, a cough analysis module 26, a restlessness analysis module 28, a blood pressure analysis module 29, and an arousal analysis module 31. For some applications, pattern analysis module includes additional modules and/or functionalities to those shown in FIG. 2. For example, pattern analysis module 16 may include one or more of the additional modules and/or functionalities shown in FIG. 4. For some applications, two or more of analysis modules 20, 22, 23, 26, 28, 29, and 31 (and/or the additional modules and/or functionalities) are packaged in a single housing. For other applications, the modules are packaged separately (for example, so as to enable remote analysis, by one or more of the pattern analysis modules, of breathing signals acquired locally by data acquisition module 20).

User interface 24 typically comprises a dedicated display unit, such as an LCD or CRT monitor. Alternatively or additionally, the user interface 24 comprises a wireless or wired communication port for relaying the acquired raw data and/or processed data to a remote site for further analysis, interpretation, expert review, and/or clinical follow-up. For example, the data may be transferred over a telephone line, and/or over the Internet or another wide-area network, either wirelessly or via wires.

Breathing pattern analysis module 22 is configured to extract breathing patterns from the motion data, as described hereinbelow with reference to FIG. 3, and heartbeat pattern analysis module 23 is configured to extract heartbeat patterns from the motion data. Alternatively or additionally, system 10 comprises another type of sensor, such as an acoustic or air-flow sensor attached or directed at the patient's face, neck, chest, and/or back, or placed under the mattress.

In some applications of the present invention, system 10 comprises a temperature sensor 80 for measurement of body temperature. For some applications, temperature sensor 80 comprises an integrated infrared sensor for measurement of body temperature. Body temperature is a vital sign indicative of general status of systemic infection and inflammation. Global rise in body temperature is used as a first screening tool in medical diagnostics.

Figure 3:
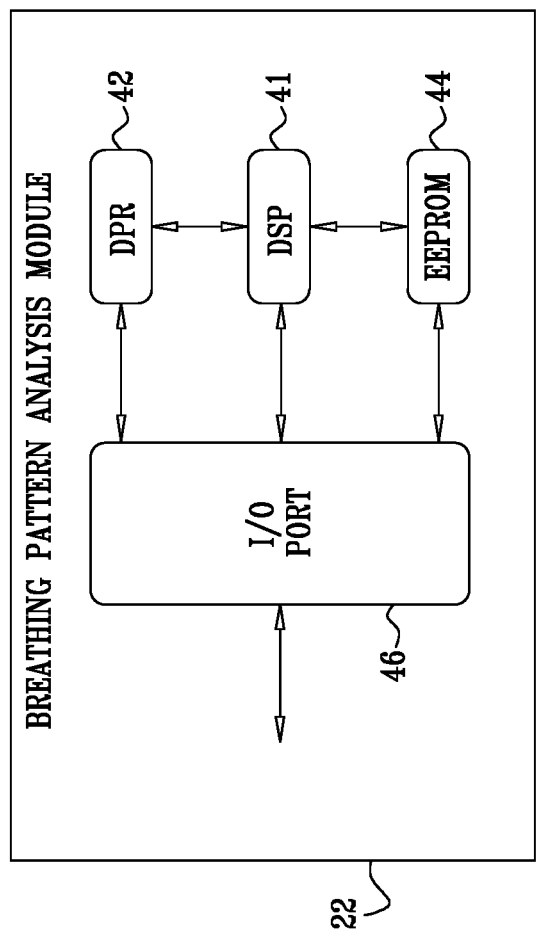
FIG. 3 is a schematic block diagram illustrating a breathing pattern analysis module of the control unit of FIG. 2, in accordance with some applications of the present invention.

FIG. 3 is a schematic block diagram illustrating components of breathing pattern analysis module 22, in accordance with some applications of the present invention. Breathing pattern analysis module 22 analyzes changes in breathing patterns, typically during sleep. Breathing pattern analysis module 22 typically comprises a digital signal processor (DSP) 41, a dual port RAM (DPR) 42, an EEPROM 44, and an I/O port 46. Modules 23, 26, 28, 29, and 31 may be similar to module 22 shown in FIG. 3. For example, modules 23, 26, 28, 29, and 31 may include a digital signal processor, a dual port RAM, an EEPROM, and an I/O port similar to digital signal processor 41, dual port RAM 42, EEPROM 44, and I/O port 46.

In some applications of the present invention, data acquisition module 20 is configured to non-invasively monitor breathing and heartbeat patterns of patient 12. Breathing pattern analysis module 22 and heartbeat pattern analysis module 23 are configured to extract breathing patterns and heartbeat patterns respectively from the raw data generated by data acquisition module 20, and to perform processing and classification of the breathing patterns and the heartbeat patterns, respectively. Breathing pattern analysis module 22 and heartbeat pattern analysis module 23 are configured to analyze the respective patterns in order to (a) predict an approaching clinical episode, such as an asthma attack, heart condition-related lung fluid buildup, sepsis, cardiac arrest, or respiratory depression, and/or (b) monitor the severity and progression of a clinical episode as it occurs. User interface 24 is configured to notify patient 12 and/or a clinician of the predicted or occurring episode. Prediction of an approaching clinical episode facilitates early preventive treatment, which generally improves outcomes, e.g., by lowering required dosages of medication, and/or lowering mortality and morbidity. When treating a hospitalized patient in a general care ward, for example, an earlier identification of patient deterioration may prevent the need to admit the patient to the ICU, shorten his length of stay, and increase the likelihood for successful recovery to discharge.

Normal breathing patterns in sleep are likely to be slow changes over days, weeks, months and years. Some changes are periodic due to periodic environmental changes, such as a change in seasons, or to a periodic schedule such as a weekly schedule (for example outdoor play every Saturday), or biological cycles such as the menstrual cycle. Other changes are monotonically progressive, for example, changes that occur as children grow or adults age. In some applications of the present invention, system 10 tracks these slow changes dynamically.

In some applications of the present invention, system 10 is configured to monitor clinical parameters of the patient including, but not limited to, breathing rate; heart rate; coughing counts; expiration/inspiration ratios; amplitude, number, or frequency of augmented breaths; amplitude, number, or frequency of deep inspirations; amplitude, duration, or frequency of tremors, duration or frequency of sleep cycles, and amplitude, number, or frequency of restlessness patterns. These parameters are examples of "clinical parameters," as used in the specification and in the claims. In general, a clinical parameter is a numerical parameter that can be measured in a clinical setting and that has clinical value. The terms "clinical parameters" and "physiological parameters" are used interchangeably in the present application.

Breathing pattern analysis module 22 and heartbeat pattern analysis module typically derive breathing patterns and heartbeat patterns from the raw data in accordance with the techniques described in US 2011/0112442 to Meger and in US 2012/0253142 to Meger, both of which applications are incorporated herein by reference. In general, system 10 is configured to monitor clinical parameters of the patient, and to generate alerts and/or reports in response thereto, in a generally similar manner to system 10 described US 2011/0112442 to Meger and in US 2012/0253142 to Meger, both of which applications are incorporated herein by reference.

In some applications of the present invention, pattern analysis module 16 combines clinical parameter data generated from one or more of analysis modules 20, 22, 23, 26, 28, 29, and 31, and analyzes the data in order to predict and/or monitor a clinical event. For some applications, pattern analysis module 16 derives a score for each parameter based on the parameter's deviation from baseline values (either for the specific patient or based on population averages). Pattern analysis module 16 optionally combines the scores, such as by computing an average, maximum, standard deviation, or other function of the scores. The combined score is compared to one or more threshold values (which may or may not be predetermined) to determine whether an episode is predicted, currently occurring, or neither predicted nor occurring, and/or to monitor the severity and progression of an occurring episode. For some applications, pattern analysis module 16 learns the criteria and/or functions for combining the individual parameter scores for the specific patient or patient group based on personal or group history. For example, pattern analysis module 16 may perform such learning by analyzing parameters measured prior to previous clinical events.

Figure 4:
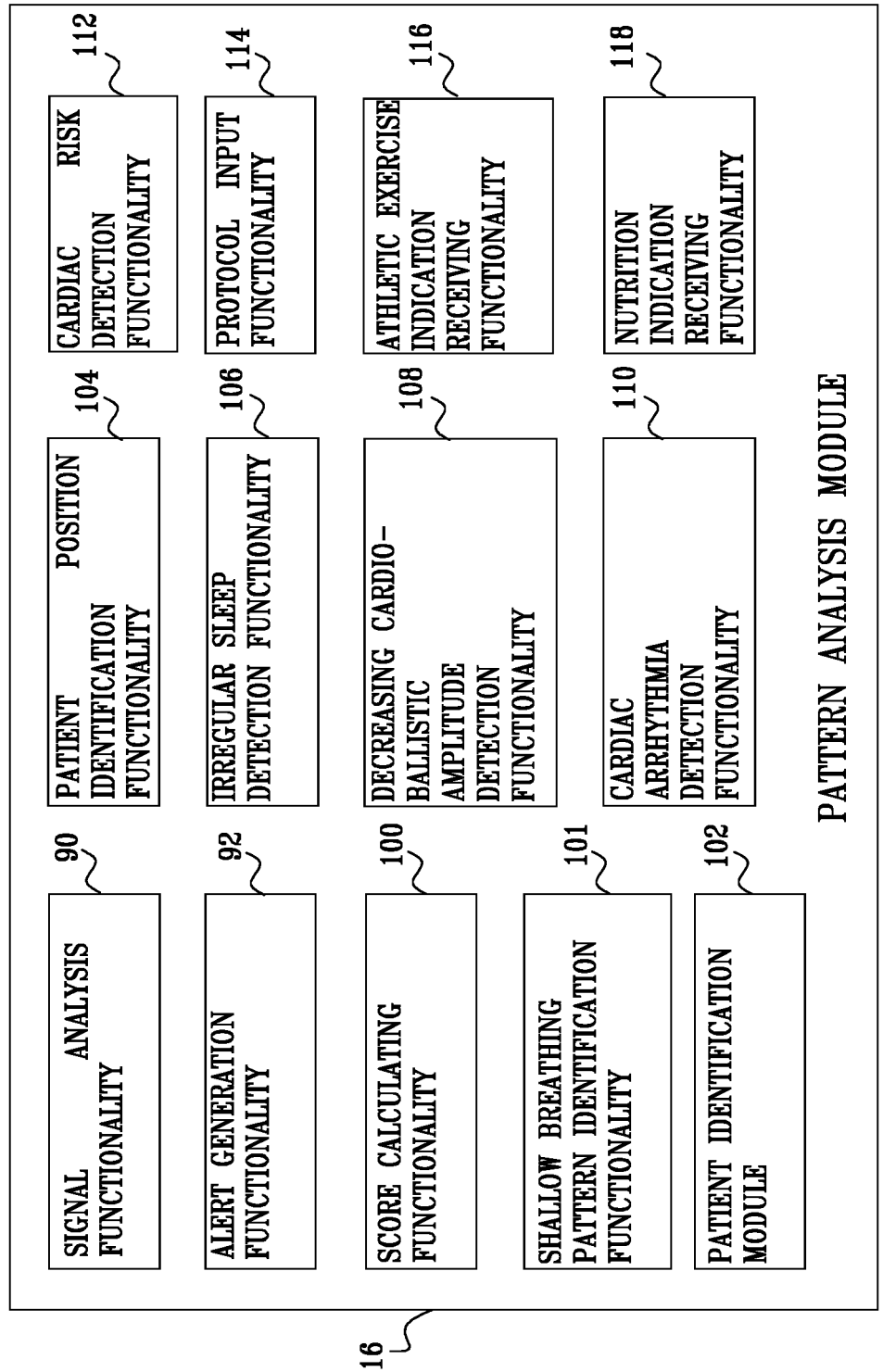
FIG. 4 is a schematic block diagram illustrating additional components of a pattern analysis module of the control unit of FIG. 2, in accordance with some applications of the present invention.

Reference is now made to FIG. 4, which is a schematic illustration of functionalities and/or modules that are included in pattern analysis module 16, in addition to the modules of the pattern analysis module that are shown in FIG. 2, in accordance with some applications of the present invention. Typically, pattern analysis module includes signal analysis functionality 90. The signal analysis functionality is configured to analyze the signals received from the sensors that provide input to control unit 14 and to determine a condition of the patient and/or generate an output (e.g., an alert), in response thereto. Many of the functionalities of control unit 14 that are described herein as being performed by pattern analysis module 16 are performed by the signal analysis functionality of the pattern analysis module. Pattern analysis module typically further includes alert-generation-functionality 92 that is configured to generate an alert in response to the signal analysis that is performed by the signal analysis functionality. For example, alerts may be generated on pagers of clinicians, at user interface (e.g., display) 24, and/or at a central monitoring system user interface (e.g., display), as described hereinbelow with reference to FIG. 5. For some applications, pattern analysis module includes score calculating functionality 100 configured to calculate a score in response to the signal analysis that is performed by the signal analysis functionality. In accordance with some applications, pattern analysis module includes additional functionalities and/or modules, such as a shallow-breathing-pattern-identification functionality 101, a patient identification module 102, a patient-position-identification functionality 104, an irregular-sleep-detection functionality 106, a decreasing-cardioballistic-amplitude-detection functionality 108, a cardiac-arrhythmia-detection functionality 110, a cardiac-risk-detection functionality 112, protocol input functionality 114, athletic-exercise-receiving functionality 116, and/or nutrition-receiving functionality 118. The functions of the additional functionalities and/or modules are described in further detail hereinbelow.

In some applications, control unit 14 (e.g., pattern analysis module 16 of the control unit) includes a score-calculating functionality 100 that is configured to calculate a score that is based on a combination of clinical parameter data generated continuously from one or more of analysis modules 20, 22, 23, 26, 28, 29, and 31, as well as data that are received periodically (e.g., at time intervals of between 0.5 hours and 12 hours). In this manner, the system calculates a dynamically changing score based in part on data that are only received periodically. For some applications, the control unit receives the data periodically via a manual input (e.g., by a clinician manually inputting the data to the control unit via the user interface). Alternatively or additionally, the periodically-received data are periodically received from an electronic medical record system, or from other sensors such as weight sensor 81 or angle sensor 87. For some applications, the periodically-received data may include patient demographic information such as age or gender, and/or a patient's manually-read vital signs such as blood pressure or temperature, and/or clinician observations such as level of consciousness.

By combining continuous readings such as heart rate or respiratory rates with constant or slower changing information such as age, gender, or temperature, a dynamic score that has been previously used as a discontinuous score is generated. For example, the Modified Early Warning Score (MEWS) used by clinicians worldwide is often based on giving point scores to manual heart rate, respiratory rate, temperature, and blood pressure spot readings. In some applications, system 10 continuously measures heart rate and respiratory rate and uses the latest spot check results of blood pressure and temperature readings (which in some cases are clinician entered) in order to generate a continuous MEWS result calculated for example every second. When this score crosses a specific threshold an alert is generated by the system. Alternatively or additionally, when the standard deviation of the score crosses a threshold, an alert is generated by the system. Alternatively or additionally, when the score changes versus the patient's baseline (which may be calculated, for example, by averaging the previous 24 hours of scores) by over a threshold percentage, e.g. 25 percent, an alert is generated by the system. For some applications, calculating a dynamically changing score based in part on data that are only received periodically provides an efficient way of combining continuous readings with spot check data and/or demographic information.

In some applications, a specific combination of score elements that are collected by variable sensors is used in a way that may be relevant to a specific condition. For example, the deterioration of a congestive heart failure patient is often characterized by one or more of changes in (a) heart rate, (b) respiratory rate, and (c) weight change. In some applications, all three of the aforementioned parameters are measured in a contact-less manner, e.g., via one or more sensors (e.g., motion sensor 30) installed in the patient's bed. For some applications, by combining the three aforementioned parameters into a score, a more specific and sensitive calculation of patient condition change is calculated. For example, the score may be calculated as: $S=5*W+3*R+2*H$ where S is the score, and W, R and H are the average nightly readings of patient's weight in pounds, respiratory rate in breaths per minute, and heart rate in beats per minute respectively. If the score changes by more than a threshold (which may be set to be between 5 and 20, for example, 10), the clinician is alerted. In some applications this score is calculated only for congestive heart failure patients. More generally, the score may be calculated as: $S=k_1*W+k_2*R+k_3*H$, where $2<k_1<10$, $1<k_2<6$, and $0.5<k_3<4$, and the score may be compared to a threshold as described above.

In some applications, the patterns analyzed by one sensor are used to enhance the accuracy of readings by another. For example, the contact-less semi-rigid piezoelectric sensing plate may be used to measure the heart rate related signal, respiratory related signal, and motion signal, and to detect the patient's posture change as described herein. By identifying that the patient has returned to the same position and only then activating the weight sensors, the system can verify that the weight measurement is always done in a similar body position and a point in time when the patient is not moving, thus increasing the accuracy of the weight measurement.

In some applications, motion sensor 30 is disposed under the mattress of the patient's bed and is combined with weight sensor(s) 81, e.g., a weight sensor embedded into a bed as manufactured by Stryker Inc. of Kalamazoo, Mich. Control unit 14 calculates the patient's weight and location of center of gravity on the bed area, based upon data received from the weight sensor. Sensor 30 detects amplitudes of vibrations at different frequencies. A significant change in the amplitudes at the different frequencies is used to identify change in patient position and/or entry or exit from bed. The pattern analysis module (e.g., signal analysis functionality 90 of the pattern analysis module) determines that the patient has undergone a position change, responsively to both the motion sensor signal and the weight sensor signal. The combination of the two sensors allows a more accurate detection of change in patient position. For example, nurses are often interested in knowing when a patient has sat up, for those patients who are at risk of fall. This provides an early indication of an increased risk that the patient may attempt to exit the bed and therefore may be at increased risk of falling. On the other hand, nurses would like to get as few false alerts as possible and therefore it is advantageous to verify that the signal from one sensing modality is verified by a signal from an additional sensing modality.

In some applications, sensor 30 detects change in frequency distribution that is characteristic of the patient's back being disconnected from the mattress. This is done by analyzing the time and/or frequency properties of the under the mattress sensor signal, measured in the two states. For example, in some applications the control unit calculates parameters that estimate the signal-to-noise ratio (SNR) in the time or frequency domain. In some applications, the amplitude of the heart pulse signal (peak to peak) in the time domain is calculated and compared to the noise level in the time domain. This SNR typically decreases by a factor of 100 when a patient sits up with his back not contacting the mattress, as compared to when he is lying in bed. Thus, a reduction by a threshold factor (for example, a factor of between 5 and 100, or approximately 20) in the SNR ratio may be identified by the signal analysis functionality as an indication that the patient has sat up. Alternatively or additionally, the signal analysis functionality analyzes the time domain component of the motion sensor signal and calculates the number of turns (i.e., the number of sign changes in the first derivative of the sensor signal) normalized by the length of the segment. This parameter is typically higher by a factor of 2 when the patient is sitting compared to when the patient is lying. Therefore an increase in this parameter by a threshold percentage level (for example, 40 percent to 90 percent, or approximately 65 percent) is identified by the signal analysis functionality as an indication that the patient has sat up.

In some applications, this indication that the patient has sat up based on the motion sensor signal, is combined with an indication of a change in the center of mass based on the weight sensor signal. For example, a change in the center of mass of 5 cm to 50 cm, e.g., approximately 25 centimeters, in the direction of the legs may be interpreted by the signal analysis functionality as an indication that the patient has sat up. For some applications, the signal analysis functionality generates an alert that is indicative of the patient having sat up, and/or of the patient being likely to leave the bed, only in response to the signals from both the motion sensor and the weight sensor indicating that this is the case. This may help to reduce false alerts, which may be generated if only one of the sensing modalities were to be used. For some applications, in response to the signals from both the motion sensor and the weight sensor (e.g., in response to the sensor signals providing indications as described hereinabove), the signal analysis functionality is configured to differentiate between the motion of just a limb and a repositioning of the patient's whole body (which may be indicative of the patient having sat up and/or being about to leave the bed).

Reference is again made to FIG. 1. As described hereinabove, motion sensor 30 is typically coupled to a resting surface upon which the patient rests. For example, as shown in FIG. 1, motion sensor 30 may be placed under a mattress of a bed, and may sense motion of the patient while the patient is in the bed, and generate a motion sensor signal in response thereto. Alternatively or additionally, as shown in FIGS. 12A-B, motion sensor 30 may be coupled to a chair (e.g., a wheelchair) upon which the patient sits, and may sense motion of the patient while the patient is sitting in the chair, and generate a motion sensor signal in response thereto. For some applications, system 10 includes a first motion sensor which is under the mattress of the patient's bed, and a second motion sensor 30, which is coupled to a chair in the patient's room. The first sensor senses motion of the patient while the patient is in the bed, and the second motion sensor senses motion of the patient while the patient is in the chair. System 10 monitors the patient responsively to both the first and the second sensor signals, as described in further detail hereinbelow.

For some applications, a plurality of motion sensors are coupled to a single resting surface, and are used as motion sensor 30. For example, two or more motion sensors that are disposed under the patient's mattress may be used as motion sensor 30. Alternatively, only a single sensor is coupled to a given resting surface. In some applications of the present invention, motion sensor 30 comprises a pressure/vibration sensor (for example, a piezoelectric sensor) or an accelerometer, which is typically configured to be installed in, on, or under resting surface 37 upon which the patient rests, e.g., sleeps, and to sense breathing- and heartbeat-related motion of the patient. For some applications, surface 37 comprises a mattress, a mattress covering, a sheet, a mattress pad, and/or a mattress cover. For some applications, motion sensor 30 is integrated into surface 37, e.g., into a mattress, and the motion sensor and reclining surface are provided together as an integrated unit. For some applications, motion sensor 30 is configured to be installed in, on, or under surface 37 in a vicinity of abdomen 38 or chest 39 of patient 12. Alternatively or additionally, motion sensor 30 is installed in, on, or under surface 37 in a vicinity of a portion of patient 12 anatomically below the patient's waist, such as in a vicinity of legs 40 of the patient. For some applications, such positioning provides a clearer pulse signal than positioning the sensor in a vicinity of abdomen 38 or chest 39 of the patient.

In some applications of the present invention, sensor 30 comprises a single piezoelectric ceramic sensor. The sensor is attached to a plate, e.g., a semi-rigid plate comprising flexible plastic (e.g. Perspex (PMMA), polycarbonate, or acrylonitrile butadiene styrene (ABS)) or non-plastics (e.g., cardboard), for example having dimensions of 20 cm×28 cm×1.5 mm. The sensor is able to detect a signal when the patient assumes most common bed postures, even when the patient's body is not directly above the sensor. In some applications, sensor 30 is implemented using two or more thin piezoelectric sensors (e.g. radius of 13 mm and thickness of 100 um), wherein the two or more sensors are stacked on top of the semi-rigid plate so that the first sensor is attached to the plate and the second (and potentially third, etc.) is attached to the first sensor. The signals from both sensors are added to each other by amplification and/or digitizing electronics, in order to increase the signal to noise ratio of the system.

For some applications, motion sensor 30 (the sensor comprising, for example, a piezoelectric sensor) is encapsulated in a rigid compartment, which typically has a surface area of at least 10 cm², and a thickness of less than 5 mm. The sensor output is channeled to an electronic amplifier, such as a charge amplifier typically used with piezoelectric sensors, and capacitive transducers to condition the extremely high output impedance of the amplifier to a low impedance voltage suitable for transmission over long cables. The sensor and electronic amplifier translate the mechanical vibrations into electrical signals.

In some applications of the present invention, breathing pattern analysis module 22 extracts breathing-related signals by performing spectral filtering in the range of about 0.05 to about 0.8 Hz, and heartbeat pattern analysis module 23 extracts heartbeat-related signals by performing spectral filtering in the range of about 0.8 to about 5.0 Hz. For some applications, motion data acquisition module 20 adapts the spectral filtering based on the age of patient 12. For example, small children typically have higher breathing and heart rates, and therefore spectral filtering is typically set more tightly to the higher end of the frequency ranges, such as between about 0.1 and about 0.8 Hz for breathing, and between about 1.2 and about 5 Hz for heartbeat. For adults, spectral filtering is typically set more tightly to the lower end of the frequency ranges, such as between about 0.05 and about 0.5 Hz for breathing, and between about 0.5 and about 2.5 Hz for heartbeat.

In some applications, system 10 includes a posture change identification algorithm that identifies whether a patient has changed his position on a bed or other reclining surface or chair. The objective is to identify whether the patient moved between 1 of the 4 positions: supine, on stomach, on left side, or on right side, since such a change every 2-4 hours is generally required in order to prevent pressure ulcer formation in high risk patients. Alternatively, the system may identify a major body movement that includes a repositioning of the torso and/or the sacrum area that is most prone to pressure ulcer development. The system identifies events of large body motion and evaluates whether they involved a posture change of the main body. For example, the system may identify a posture change using techniques as described in WO 09/138976 to Meger, which is incorporated herein by reference.

In some applications the sensor is placed in a chair on which a patient is sitting. The system detects a significant change in the weight distribution on the chair in order to help the clinicians prevent pressure ulcers. The system identifies events of large body motion and evaluates whether they involved a significant change in body position that changes the weight distribution on the chair—for example from leaning on the right side of the chair (possibly with the support of a pillow) to the left side. In some applications, the nurse manually indicates to the system that the patient has been repositioned on the chair and the system verifies that a simultaneous significant motion has been detected by the sensor. In some cases, clinicians request an alert as frequently as every 15 minutes to reposition the patient in the chair in order to prevent pressure ulcers while sitting.

In some applications, a clinician can activate a turn protocol on system 10, whereby the system will remind the clinician to perform a patient turn (posture change) every predetermined threshold period of time (usually between 2 to 4 hours). System 10 displays a counter of time since the last time a clinician turned the patient and when the time reaches the above threshold, the system alerts the clinician to turn the patient. The clinician in some applications has an input means to indicate that the patient was actually turned and system 10 then verifies that the turn was actually detected by the mechanical sensor (a video sensor may also be used). All times of patient turns by clinicians are documented as well as an indication of whether the clinician's indicated turn was verified by system 10 through its sensor. If one or more turns were not verified, the system also has the option to alert a clinician. In addition, in some applications, if the clinician has activated a turn protocol and the system has detected a patient's posture change without an indication being received from the clinician that the patient was turned by a clinician, the system identifies that an autonomous turn was performed by the patient. In such a case, the system may indicate that information to the clinician for him to consider whether there is a need to turn the patient at the next scheduled time and/or to re-evaluate (using for example standard scales such as Norton or Braden) whether the patient needs to be maintained on a turn protocol. For some applications, this may prevent a clinician from turning a patient unnecessarily, which can be heavily labor intensive.

In some applications, the system automatically calculates a score similar to Norton or Braden based on continuously collected data on patient motion and other data that may be manually entered by the clinician, read automatically from an Electronic Medical Record system, or collected by additional sensors. For example, one component of the Braden score is the degree to which the patient's skin is exposed to moisture. In some applications, system 10 includes moisture sensor 85, sensor 85 being placed in or at the bed or on the patient's body. The moisture reading is processed by the processing unit in calculating an overall pressure ulcer risk score similar to the Braden scale score. In some applications, the score is calculated every time one of the parameters has a new reading (e.g. every 1 minute if a new motion reading is available every 1 minute) or every pre-set time period such as once an hour. If a significant change in the score, a trend, or a crossing of a threshold is identified, a clinician is alerted.

In some applications, system 10 is utilized to reduce patient falls by driving the output unit to generate an alert when a patient sits up in bed, thus providing an early warning for the clinical team for a patient who may be leaving bed to enable assisting him before he actually leaves bed and thus prevent falls effectively. For some applications, system 10 identifies that the patient has sat up in bed in response to ongoing calculation of the noise level in the motion signal, as described hereinabove.

For some applications, system 10 is designed to predict the likelihood of a patient getting out of bed in order to provide an early warning indication. For some applications, this prevents falls that are due to healthcare professionals not being able to respond quickly enough to an alert that is issued in response to detecting that the patient has sat up, or has actually exited his bed.

Clinical studies have shown that a patient's getting out of bed is very frequently correlated with the need to go to the bathroom. For some applications, system 10 detects parameters that indicate that patient 12 may be getting out of bed in order to alert and prevent an unescorted bed exit, by detecting parameters that indicate that the patient may need to go to the bathroom, or by detecting other parameters that are indicative of an imminent bed exit by the patient.

For some applications, at least one of the following parameters is detected by the system:
- a patient not having been out of bed for a period of time higher than a threshold,
- a patient showing a higher restlessness level than a threshold or a previous baseline,
- a patient sitting up in bed,
- a patient not having been visited by a nurse for a specific period of time,
- the time of day, with respect to a patient's sleep cycle,
- the time of day,
- amount of time since patient was under anesthesia or since patient got out of surgery, and/or
- a change in the heart rate or respiration rate of the patient.

System 10 detects a likelihood of imminent bed exit at least in part responsively to one or more of the above parameters. For example, if the patient shows a higher level of restlessness or an increase in heart rate, or a combination of the two, this may be interpreted by the system as indicating that the patient is becoming less restful and the nurse may need to be called as the patient may be close to trying to get out of bed, for example, because the patient may feel the need to go to the bathroom. For example, system 10 may have a plurality of sensitivity levels for detecting the patient exiting the bed or getting ready to exit the bed. System 10 changes the sensitivity level based, for example, on the amount of time since the patient has last gotten out of bed, or was last visited by a nurse. Thus, for example, if the patient has not been out of bed for a given period of time, e.g., for over three hours (or a different period of time, e.g., five hours, or eight hours), the bed exit sensitivity level is automatically increased to a higher level. Alternatively or additionally, if on the previous day the patient got up at a given time (e.g., 5:00 AM), or if on the previous three days the patient got up at approximately the same time (e.g., at around 5:00 AM), then the bed exit sensitivity level is automatically increased prior to that time (e.g., 15 minutes prior to the time, at 4:45 AM). Further alternatively or additionally, if the nurse has not logged that he/she has visited the patient's room for a given period of time (e.g., for more than two hours) the bed exit sensitivity level is automatically increased. In some applications, if one or more of the above listed criteria is true the system alerts the clinician that the probability of a bed exit is high. For some applications, the system learns the motion patterns and vital sign patterns prior to a patient getting out of bed from previous days and interprets similar patterns as being indicative of an impending bed exit.

In some applications, system 10 reminds the nurse to take the patient to the bathroom every set amount of time (e.g. between one and six hours, for example three hours). The system detects that the patient has been taken out of bed by either or both of the nurse communicating that through the user interface module or by detection of the patient exiting the bed. Upon that detection the counter is reset. In some applications, when the counter reaches the set level, the nurse is not immediately notified to take the patient out of bed and to the bathroom. Rather, a notification is only sent if one or more of the above listed criteria is detected, such as an increase in patient motion, heart rate, the patient sitting up, the patient waking up, etc. For some applications, not immediately issuing a notification to the nurse increases comfort of the patient, for example, by avoiding the patient being woken up from a deep restful sleep in order to be taken to the bathroom. At the same time, by issuing the notification upon one or more of the above listed criteria being satisfied, patient safety is maintained, because the nurse is called to take the patient out of bed in response to the system detecting an indication that patient may be getting restless.

For some applications, system 10 is utilized to detect the change in the body temperature of patient 12, for example, by using a contact-less heat flow sensor such as that described in US 2010/0215074 to Lozinski et al., which issued as U.S. Pat. No. 8,016,480 and is incorporated herein by reference, or by using alternative temperature sensors. For some applications, the objective of such a system is to detect the patient's body temperature, and generate an alert in response to temperature changes in the patient's body, while reducing the generation of false alerts. For some applications a heat flow sensor is used as temperature sensor 80.

In some implementations, the use of the above mentioned heat flow sensor or alternative temperature sensors placed under the sheet or mattress of a bed on which the patient is lying may produce false temperature change readings. For example, a patient's change in posture may affect the heat flow detected by the sensor, and therefore provide a false alert of a change in temperature. For some applications of the present invention, in order to reduce the number of false alerts, the reading of the heat flow sensor is correlated with the reading of a motion, position and/or heart rate sensor. For example, a sensor under the mattress or a camera that detects the patient's posture change is used to detect whether the patient changed position in correlation with the temperature change detected by the heat flow sensor. If no posture change is detected, then the detected temperature change is communicated to the clinician, and/or an alert is generated. If a change of posture is detected, then, in at least some cases, the system interprets the change in posture as having caused the detected temperature change, and the detected temperature change is filtered out.

Alternatively or additionally, a sensor, such as the motion sensor under the patient's mattress, is used to continuously monitor the patient's heart rate. If the change in heat flow reading positively correlates with a change in heart rate, this is interpreted by the system as indicating that the patient has undergone a temperature change, and the temperature change is communicated to the clinician, and/or an alert is generated. Otherwise, the detected temperature change is filtered out. For some applications, instantaneous readings of the temperature sensor (e.g., the heat flow sensor) and/or heart rate sensor are used to determine whether the patient has undergone temperature changes, as described. Alternatively, the temperature sensor (e.g., the heat flow sensor), and/or heart rate sensor readings are averaged over a time period in the range of 30 seconds to 60 minutes, in order to determine whether the patient has undergone temperature changes, thereby reducing the generation of false alerts that may result from instantaneous changes in the patient's temperature and/or heart rate.

For some applications, a change in temperature (e.g., a change in heat flow), if correlated with a patient's motion or detected posture change, is used by the control unit as an indication that the posture of the patient has changed. For some applications, a significant drop in the heat flow, if correlated with a patient's motion, is used by the control unit as an indication that the patient has left the bed, and is used in a decision block process (e.g., as described herein) to determine whether the patient has exited the bed.

In accordance with the above, for some applications, pattern analysis module 16 (e.g., signal analysis functionality 90 of the pattern analysis module) is configured to receive data from motion sensor 30, angle sensor 87, and/or temperature sensor 80. The signal analysis functionality derives the patient's heart rate from the motion sensor signal, and derives the tilt angle of the bed (or a portion thereof) from the angle sensor. In response to the derived heart rate (e.g., an increase in the derived high heart rate), the signal analysis functionality determines that an alert should potentially be generated. Alternatively or additionally, in response to the temperature sensor signal (e.g., in response to the temperature sensor signal indicating that the patient's temperature has increased, which is indicative of the patient's heart rate having increased), the signal analysis functionality determines that an alert should potentially be generated. However, in response to the derived tilt angle the pattern analysis functionality withholds generating the alert, since the potential alert event (e.g., the increase in heart rate, or temperature) is interpreted as having been caused by the angle at which the patient is lying having changed. In general, the scope of the present invention includes signal analysis functionality that (a) receives a signal from angle sensor 87, (b) derives a tilt angle of the patient's bed (or other resting surface upon which the patient rests) from the angle sensor signal, and (c) withholds generating an alert that would otherwise have been generated, in response to the tilt angle of the patient's bed. The alert is withheld because the potential alert event is interpreted as having been caused by the angle at which the patient is lying having changed.

In some applications, system 10 is designed to identify possible indications of patient's temperature change without actually measuring temperature. For example, change in heart rate is often indicative of patient's temperature change but may be caused by activity level changes, body angle changes, medication or food. Thus, for some applications, signal analysis functionality 90 is configured to determine that the patient's temperature has risen by detecting an increase in the patient's heart rate. For some applications, the signal analysis functionality is configured to determine that a potential high-temperature alert event has taken place, in response to identifying that an increase in the patient's heart rate has occurred. For some applications, in response to identifying that an increase in the patient's heart rate has occurred, the signal analysis functionality generates an output indicating that the patient's temperature has risen, even without the system directly sensing the patient's temperature. For example, the signal analysis may generate an alert recommending that the patient's temperature be checked by a clinician, in response to identifying that an increase in the patient's heart rate has occurred. For some applications, in such a situation, the signal analysis functionality is configured to withhold generating the alert, in response to receiving data indicating that the tilt angle of the patient's bed has changed, that the patient has undergone motion (e.g., large body motion), and/or that medication and/or food has been administered to the patient, in a manner that may have caused the patient's heart rate to increase without the patient's body temperature having changed.

In some applications, system 10 collects some or all of the following information: heart rate, patient motion, bed angle, timing of medication and/or meals intake. If the system identifies a heart rate change for a period of time that is several minutes or hours (5 minutes to 6 hours, for example 30 minutes) and does not identify that in this time period there was a change in motion level, bed angle, food or medication, the system alerts a clinician that temperature change may have taken place and it is recommended to measure the patient's temperature directly.

In some applications, system 10 is connected to a smart bed system with an active surface, such as the InTouch Critical Care Bed with an XPRT enabled active surface made by Stryker Medical of Kalamazoo, Mich. The bed is motorized and is able to provide, for example, the following interventions: change the backrest angle, rotate the patient, and/or provide vibration and percussion treatment. System 10 activates one of these interventions in response to the clinical parameters measured. For example, if an increase in the average respiratory rate over a period of 5 minutes to 3 hours (for example 30 minutes) is identified without a corresponding increase in the patient's activity level, which may indicate a deterioration of a patient's respiratory condition, the vibration and percussion treatment is activated or the backrest angle is increased to 30 degrees. Alternatively, if the patient's number of posture changes per time has been below a threshold for a period of time between 1 hour and 24 hours (for example 3 hours), the active surface rotates the patient. Without sensing the patient's rotation, the bed would have to turn the patient every 3 hours, even if he turned autonomously, thus potentially creating a significant and/or unnecessary discomfort to the patient.

In some applications, system 10 integrates with a resting surface that has an intervention mechanism to intervene upon the patient environment, for example a motorized home electric bed such as provided by for example Leggett and Platt of Carthage, Mo., or with a reclining, motorized chair. In accordance with respective applications, the intervention mechanism may include an intervention mechanism that controls an angle of a portion of the resting surface upon which the patient lies, and/or an intervention mechanism (such as an electric blanket, or a heating or air conditioning system) that controls the temperature in the vicinity of the resting surface.

For some applications, in order to maximize the patient's quality of sleep, pattern analysis module 16 of system 10 (e.g., signal analysis functionality 90 of the pattern analysis module) identifies a sleep condition of the patient (e.g., by identifying that the patient is asleep, or by identifying a current sleep stage of the patient) by analyzing the signal from sensor 30. In response thereto, the pattern analysis module (e.g., signal analysis functionality 90 of the pattern analysis module) automatically changes a parameter of the intervention mechanism, such as to optimize sleep quality by sleep stage. For example, for some people the risk of sleep apnea events is higher during REM sleep. Therefore, in response to identifying that the patient is currently in REM sleep, the signal analysis functionality instructs the bed to automatically elevate the backrest in order to reduce the risk of sleep apnea or to activate a motor in order to turn the patient on his side since the risk of apnea is lower when a patient is sleeping on his side and not on his back. In addition, during REM sleep a person is usually less able to control his body temperature and may feel cold. Therefore, in response to identifying that the patient is currently in REM sleep, the signal analysis functionality instructs an intervention mechanism that controls the temperature in the vicinity of the patient's bed to adjust the temperature.

For some applications, pattern analysis module (e.g., signal analysis functionality 90 of the pattern analysis module) detects the body posture of the patient in bed or in a chair, i.e. whether the patient is lying on his back, left side, or right side. For some applications, this is implemented via an accelerometer worn on the patient's body, e.g., on the patient's chest, via a camera, or via a contact-less motion or weight distribution sensor under the mattress. For some applications, in order to ensure accuracy of the body posture detection mechanism, the patient initially goes through a calibration process during which he lies in bed for a period of time of several seconds to several minutes and indicates to the system in which body posture he is lying. This is used as reference to compare with signals later collected during sleep in order to accurately determine the body posture: left side, right side, on back, or on stomach.

For some applications, in response to the detected body posture, the pattern analysis module (e.g., signal analysis functionality 90 of the pattern analysis module) automatically changes a parameter of the intervention mechanism. For some applications, the signal analysis functionality automatically changes a parameter of the intervention mechanism in response to both the patient's body posture and a sleep condition of the patient (e.g., a sleep stage of the patient, such as REM sleep). For example, if the patient is in REM sleep and is lying on his back, the system may activate a motor that is intended to turn the patient on his side. Alternatively if the patient is lying on his back and is asleep and the patient is known to have blood circulation problems, the system may instruct the bed to elevate the patient's feet. In some applications these changes are not activated if the patient lying in bed but not sleeping, such as to provide comfort to the patient.

In some cases the patient is monitored for heart, respiratory rate and motion, and the pattern analysis module (e.g., signal analysis functionality 90 of the pattern analysis module) detects changes in parameters that may indicate an upcoming incontinence event such as increased heart rate and restlessness. For some applications, if such a possible upcoming incontinence event is identified the system activates an alarm to wake the patient or alert a clinician. Alternatively or additionally, in response to detecting an upcoming incontinence event, the signal analysis functionality changes the bed angle to an angle that reduces the risk of incontinence, for example a flat angle. In some cases, an incontinence warning alert is generated only if the patient has not left bed for more than a set period of time (for example, 4 hours).

In some applications, system 10 is intended to identify the respiratory pattern of a patient and detect the expiration and inspiration components of each respiratory cycle. This is useful in a clinical environment in order to calculate expiration inspiration ratio, and in addition while performing medical imaging processes such as CT scanning or MRI scanning in order to perform respiratory gating. In some applications, utilizing a contact-less under the mattress semi-rigid sensor plate, there may be a difficulty in identifying the expiration and inspiration elements of each respiratory cycle, because the directionality of the detected signal by a sensor (e.g. piezoelectric) may depend on the exact location of the patient versus the sensor. For some applications, in order to overcome this, the pattern analysis module (e.g., signal analysis functionality 90 of the pattern analysis module) may be configured to identify a time period of between 5 sec and 20 sec during which the patient is holding his breath. In response thereto, the signal analysis functionality identifies respiratory motion of the patient that immediately preceded the time period as being inspiration-related respiratory motion, and respiratory motion of the patient that immediately followed the time period as being expiration-related respiratory motion. Subsequently, the pattern analysis module (e.g., signal analysis functionality 90 of the pattern analysis module) identifies that the patient is inspiring and expiring, based upon the identified inspiration-related respiratory motion and the identified expiration-related respiratory motion.

For example, in some applications, the patient is asked (e.g., is automatically asked by system 10) to take a deep breath and hold that breath and then slowly exhale. A clinician marks the general area point of the breath-holding, or the system may identify that area automatically based on a period of between 5 sec and 20 sec within the signal in which no respiratory related motion is identified. The segment just before this breath-holding period is identified as inspiration and the period after as expiration. From that point on, as long as the patient does not change position, the system identifies the directionality of the expiration and inspiration, based upon the motion signal that was detected around the breath-holding event.

For some applications, during a calibration period (e.g., when the patient is first placed in the bed), a clinician observes the patient breathing. The clinician indicates to the system when the patient in undergoing one or more phases of the patient's respiratory cycle. For example, the clinician may press a first button on the user interface to indicate that the patient is inhaling, and/or may press another button on the user interface to indicate when the patient is exhaling. Subsequently, as long as the patient does not change position, the system identifies the directionality of the expiration and inspiration, based upon the motion signals that were detected during respective phases of the patient's breathing cycle during the calibration period.

Alternatively or additionally, heart rate generally increases during inspiration and decreases during expiration. Therefore by analyzing the average heart rate in the two sections of the breathing cycle over several cycles (such as 3 to 20 cycles, for example 8 cycles), the section with a higher heart rate is identified as the inspiration and the section with the lower heart rate is identified as the expiration. The heart rate measurement is performed either by the same motion sensor or sensor plate, or via a separate sensor such as an oximetry sensor. For some applications, pattern analysis module 16 (e.g., signal analysis functionality 90 of the pattern analysis module) is used to identify the expiration and inspiration segments of the breathing cycle, for example using one or more of the aforementioned techniques. Pattern analysis module 16 is configured to repeatedly identify the expiration and inspiration periods of the breathing cycle at a given time interval (for example, the system may be configured to repeat the identification between every 30 seconds and every 10 minutes, e.g., every minute). Alternatively or additionally, system 10 is configured to repeat the identification of the expiration and inspiration periods of the breathing cycle in response to the system detecting substantial motion of the patient, such substantial motion of the patient typically being indicative of a possible change in position of the patient with respect to the sensor.

For some patients, it is useful to identify an instability in the heart rate that may be an indication of cardiac arrhythmia. In some cases, alerting a clinician on every event of high heart rate variability may cause an unacceptable level of false alerts, as many such events may be caused by patient motion or agitation. In some applications, system 10 monitors heart rate and respiration rate. If over a significant period of time (e.g., between 1 minute and 1 hour, for example, 15 minutes) the respiratory rate is stable (for example, the standard deviation of the respiratory rate readings is less than 5 percent of the average rate for that time period) and there is no large body motion detected and the heart rate shows high variability (for example, the standard deviation of the heart rate readings is more than 8 percent of the average for that time period and there is no trend of decrease or increase in heart rate), this may be an indication for an unstable heart rate, e.g., atrial fibrillation. System 10 then alerts of an unstable heart reading and in some applications additionally displays a recommendation to the clinician to connect the patient to an ECG device.

Reference is again made to FIG. 2. In some applications of the present invention, motion sensor 30 communicates wirelessly with control unit 14. In such applications, motion sensor 30 comprises or is coupled to a sensor wireless communication module 56, which wirelessly transmits and/or receives data to/from a control unit wireless communication module 58 that is coupled to control unit 14. The communications modules communicate using a signal that is analog (e.g., using standard AM or FM), or digital (e.g., using the Bluetooth® protocol). For example, in a hospital setting, a patient site such as a bed is typically occupied by each patient for only a few days. In some cases, it may be useful to replace sensor 30 whenever a new patient is assigned to the bed. In some cases, time spent by a nurse can be reduced by placing under a mattress a pad comprising sensor 30 and wireless communication module 56. The use of such a wirelessly-enabled sensor pad eliminates the need to connect and disconnect cables from control unit 14. Such use also makes the nurse's, physician's and patient's approach and/or entry into the bed more convenient. In applications in which sensor 30 operates wirelessly, the sensor, or a sensor assembly that comprises the sensor and the wireless communication module, typically comprises an internal power source, such as a battery. In order to preserve battery life, sensor 30 typically initiates communication upon detection of a relevant motion signal or other input. For some applications, a radio-frequency identification (RFID) element is coupled to the patient, the sensor, the resting surface, and/or the user interface. The RFID elements are used to facilitate communication between the patient, the sensor, and the user interface. For some applications, the RFID elements comprise a portion of a location-sensing system, as described in further detail hereinbelow.

In some settings, for example in hospitals, a plurality of systems 10 may be used in relatively close proximity (e.g., as described hereinbelow with reference to FIG. 5). In such scenarios, each control unit 14 typically communicates only with the correct motion sensor 30 and not erroneously with another motion sensor 30 positioned at a different bed and associated with a different system 10. Bluetooth protocols, for example, allow for such pairing processes. In some applications, the system performs such pairing without initiating a conventional Bluetooth-type pairing process on both the sensor side and the control unit side. In addition to wirelessly-enabled motion sensor 30, control unit 14 is coupled to one or more contact sensors applied to patient 12, such as a blood oxygen monitor 86 (e.g., a pulse oximeter/photoplethysmograph), an ECG monitor 62, or a temperature sensor 80. Control unit 14 extracts pulse information from the contact sensors. In order to identify the paired motion sensor 30 among several such transmitting motion sensors 30 within wireless range of the control unit, the control unit calculates the pulse data from each wireless signal received from a motion sensor 30 and identifies a signal that has pulse data that correlates with information received from contact sensors. Upon identifying such a match, the control unit records identifying features of the wireless communication module 56 coupled to the identified motion sensor 30 (e.g., a transmitter unique ID), such that from that point onward the identified sensor 30 is paired to control unit 14. For some applications, upon performing such pairing, control unit 14 notifies a clinician that contact sensors are no longer required and that the patient can be monitored with contact-less sensor 30 only, or with fewer contact sensors.

For some wireless applications, upon activation of sensor 30, the nurse presses a connect button on control unit 14 and taps one or more times on sensor 30. Control unit 14 then connects to the one of a plurality of sensors 30 in the vicinity which transmits the taps at that exact point in time. Alternatively, user interface 24 provides a visual or audio indication of the taps, and the clinician verifies that his or her taps are correctly displayed before approving the pairing of the sensor to the control unit. For some applications, the sensor, including the sensor plate, as described hereinbelow, does not comprise any buttons or other user controls. (These applications do not exclude the use of an on/off switch on wirelessly-enabled motion sensor 30.) For some applications, wirelessly-enabled motion sensor 30 is activated and paired with control unit 14 without requiring the pressing of any buttons or controls on the sensor. Instead the sensor is activated and paired either by tapping on the sensor or by temporarily connecting the sensor to the control unit with a wire. For some applications, a temporary cable is used to initiate the pairing of sensor 30 and control unit 14. After the sensor and control have been paired, the temporary cable is disconnected and the system operates using wireless communication. Alternatively or additionally, a motion sensor (e.g., a pressure sensor) coupled to control unit 14 by a wire is briefly placed on the reclining surface and pressed down against the mattress. The simultaneous readings from the wired motion sensor and from wirelessly-enabled motion sensor 30 enable control unit 14 to identify the particular wirelessly-enabled motion sensor 30 that is under the mattress that was pressed.

Figure 5:
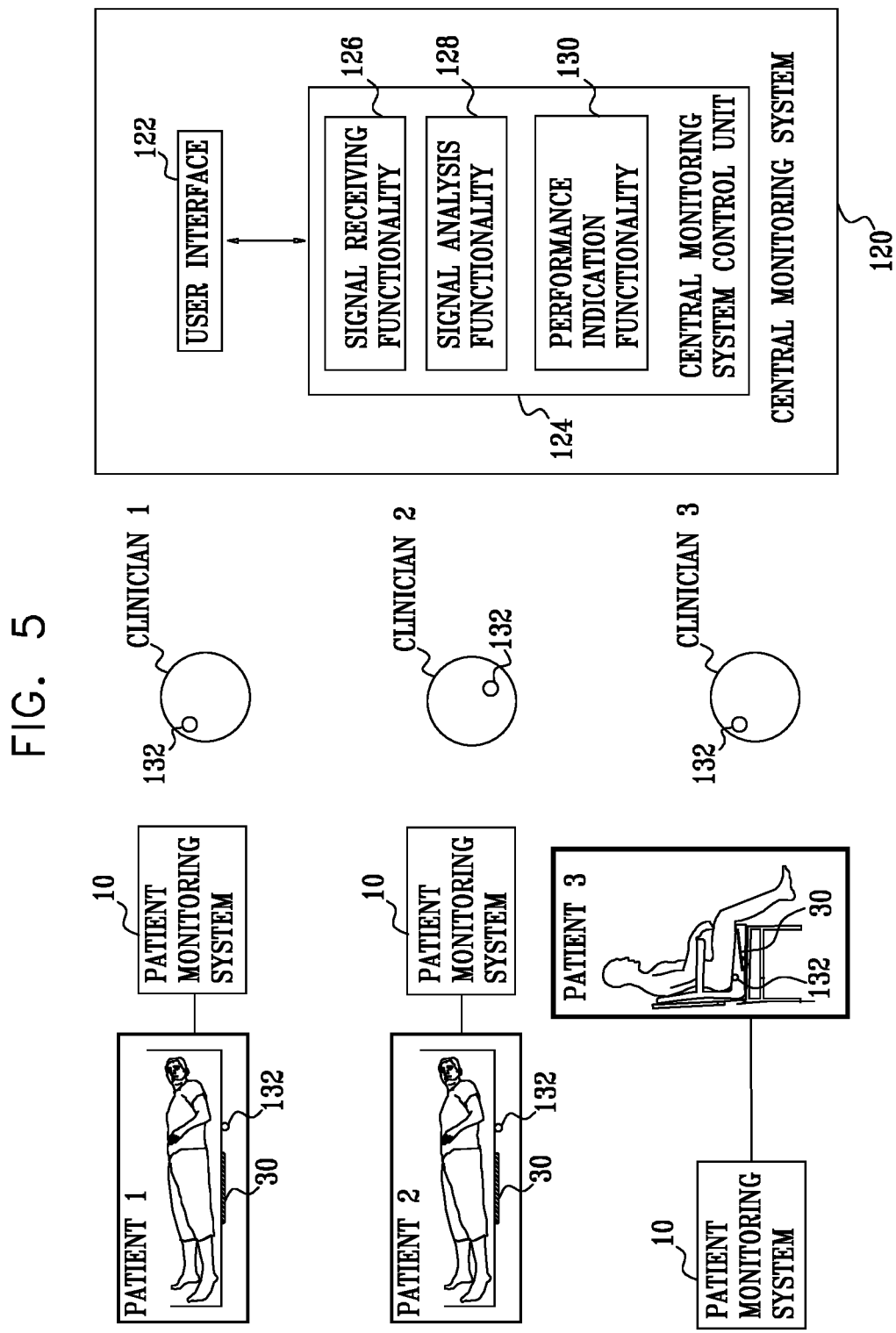
FIG. 5 is a schematic illustration of a plurality of patient monitoring systems, which are in communication with a central monitoring system, in accordance with some applications of the present invention.

Reference is now made to FIG. 5, which is a schematic illustration of a plurality of patient monitoring systems 10, which are in communication with a central monitoring system 120, in accordance with some applications of the present invention. As described hereinabove, in some settings, for example in hospitals, a plurality of patient monitoring systems may be used in relatively close proximity. For example, there may be a patient monitoring system associated with each of the beds in a ward, and the patient monitoring systems of all of the beds on the ward may communicate with a central monitoring system that may be near the nurses' station. For some applications, local patient monitoring systems are located in respective patients' homes and central monitoring system 120 is located at a call center. Typically, the central monitoring system includes a central monitoring user interface 122 (e.g., a display), and a central monitoring system control unit 124. The central monitoring system control unit typically includes signal receiving functionality 126 and signal analysis functionality 128 configured to analyze the received data. The display typically displays data relating to a plurality of the patients the monitoring systems of whom are associated with the central monitoring system. For some applications, motion sensor 30 (and/or the other sensors described hereinabove) of the individual patient monitoring systems, communicate directly with the central monitoring system control unit. Alternatively or additionally, control units 14 of the individual patient monitoring systems communicate with the central monitoring system control unit.

As shown in FIG. 5, some of the patients (e.g., patients 1 and 2 in FIG. 5) may be in beds and may have patient monitoring systems 10 associated with their beds. Other patients (e.g., patient 3) may be sitting on a chair (e.g., a wheelchair) and there may be a patient monitoring system 10 associated with the chair. Typically, each of the individual patient monitoring systems 10 function generally in accordance with the functionalities of patient monitoring system 10 described herein. For some applications, each of the patient monitoring systems has a user interface 24 (e.g., a display) associated with the patient monitoring system, as described hereinabove.

In monitoring systems in acute or long term care institutions it is generally valuable to identify events when clinical intervention helped prevent deterioration. This is useful in order to share learning with other staff and to recognize staff members as having achieved effective patient care, in order to motivate staff to provide consistent high quality care. In some applications, system 10 is utilized in order to analyze patient situation and identify alert conditions and then identify when patient trends or number of alert conditions improve for the better after clinicians responded to alerts in a timely manner. For example, system 10 may analyze patient trends and identify a trend of decreasing respiratory rate that reaches respiratory rates that are lower than 8 breaths per minute. This may indicate that the patient is in risk of respiratory depression. The system generates an alert in response to detecting such trends, and measures the amount of time until the clinician responds to the alert. The amount of time taken until the clinician responds to the alert may be measured by measuring the time from when the alert is communicated to the clinician until the system determines that the clinician has responded to the alert The system may determine that the clinician has responded to the alert based upon an input by the clinician via user interface (e.g., display) 24. Alternatively, the system may determine that the alert has been responded to based upon the sensor signal associated with the patient indicating that a clinical parameter of the patient has changed in a manner that is indicative of a clinician having attended to the patient. If the response to the alert is performed in a period of time that is below a threshold (e.g., 30 seconds to 300 seconds, for example, 60 seconds), and if, following the alert response, system 10 detects a clear change in trend, for example in this case the respiratory rate increases towards normally expected readings (e.g. higher than 10 breaths per minute), then system 10 documents this event and communicates it to a manager. The manager may then utilize this information to recognize the clinician who effectively responded. Alternatively or additionally, system 10 may communicate, to a manager, events when alerts have not been responded to in a timely way or in a way that positively improved patient conditions. Alternatively or additionally, system 10 may utilize data available in electronic medical record systems in order to identify if following an alert by the system, a medical intervention or further diagnostics was performed. In a time when medical staff is often limited in number, providing managers with effective tools to identify quality interventions, and, on the other hand, to identify learning opportunities, may enable improved and a more consistent quality of care.

In accordance with the above-described applications, for some applications the signal analysis functionality of the local patient monitoring systems 10, or of the central monitoring system 120 is configured to determine a response time of a clinician to an alert that was generated in response to a sensor signal corresponding to a given patient. The signal analysis functionality is configured to determine changes in the physiological parameters of the given patient that are likely to have been caused by the response of the clinician to the alert. In response thereto, the signal analysis functionality generates an output that is indicative of a correlation between an improvement in the patient's condition, and the clinician response time having been low. Alternatively, the signal analysis functionality generates an output that is indicative of a correlation between the patient's condition not having improved, and the clinician response time having been high. In accordance with respective applications, the aforementioned outputs are generated at the local patient monitoring systems, or at the central monitoring system (e.g., such that the output is available to a manager).

For some applications, signal analysis functionality 128 of the central monitoring system control unit 124 collects statistics from each of the local patient monitoring systems relating to the response times of clinicians to alerts. In response thereto, performance indication functionality 130 of the central monitoring system control unit generates an indication of a performance level of the clinicians. For some applications, the clinician performance level is measured with respect to a standard performance level. For example, average information from peer sites (for example, different hospitals or different units in a hospital), the peer sites typically having similar patient monitoring systems to each other, may be compared and averaged. Or, the clinician performance level may be compared to an average historic performance level over a given time period. Typically, reports are generated based upon the clinician performance level. For example, a daily or weekly e-mail may be sent to predefined managers' e-mail addresses regarding how clinician performance levels at a specific site compares to peer sites, to its own history and to its defined targets. For some applications, as a clinician is assigned to each patient, response times and other protocol performance per clinician is calculated (for example, how many times each patient was taken out of bed in general or moved into a chair with a chair sensor). This information is sent to a manager and may also be compared to information pertaining to peers, previous history and set targets. This typically helps to empower managers to lead their clinical team more effectively to meet protocol performance targets.

In some applications, the control unit identifies a historical alert-response time, e.g., an average response time over a previous period of time, for each of the clinicians. The historical alert-response times are then used to guide subsequent alert-generations, as described immediately hereinbelow.

Clinical sensor 30 measures a clinical parameter of a patient, and generates a clinical-sensor signal in response thereto. When the control unit determines, in response to the clinical-sensor signal, that an alert event has occurred, the control unit identifies a subset of the clinicians in response to the historical alert-response times, and communicates an alert to the identified subset of clinicians before communicating the alert to any other clinician. In some applications, the control unit identifies a subset of the clinicians whose respective historical alert-response times are less than the historical alert-response time of at least one clinician who is not a member of the subset. In other words, the control unit is "biased" toward alerting those clinicians who historically have responded more quickly to alerts, in order to help the patient receive attention as quickly as possible. In other applications, the control unit identifies a subset of the clinicians whose respective historical alert-response times are greater than the historical alert-response time of at least one clinician who is not a member of the subset. In other words, the control unit is biased toward alerting slower clinicians, in order to help train these clinicians to respond more quickly, and/or to provide incentive for clinicians to respond quickly to alerts. (The incentive is the "reward" of not being alerted.)

The table below shows an example scenario in which a plurality of clinicians have different respective historical alert-response times.

TABLE 1

| Clinician | Historical Alert-Response Time (AU) |
| --- | --- |
| A | 3 |
| B | 5 |
| C | 6.5 |
| D | 2 |
| E | 4 |
| F | 7 |
| G | 8 |

Ordered by historical alert-response times, the clinicians in Table 1 may be listed as D, A, E, B, C, F, and G. Per the description above, the control unit may identify (for example) the subset consisting of D, A, and E, whose historical alert-response times are less than those of the other clinicians. Alternatively, the control unit may identify (for example) clinicians C, F, and G, whose historical alert-response times are greater than those of the other clinicians. (If the identified subset does not respond within a given period of time, the control unit may then alert other clinicians who are not members of the subset.)

In some applications, the identification of the subset of clinicians is in response to other factors, in addition to the historical alert-response times. For example, the control unit may compare the severity of the alert event to a threshold, and identify the subset of the clinicians in response to the comparison and in response to the historical alert-response times. For example, the control unit may identify the "quick" clinicians (i.e., the clinicians whose respective historical alert-response times are less than the historical alert-response times of one or more of the other clinicians) if the severity of the alert event is greater than the threshold, and the "slow" clinicians (i.e., the clinicians whose respective historical alert-response times are greater than the historical alert-response times of one or more of the other clinicians) if the severity of the alert event is not greater than the threshold. With reference to Table 1, if the severity of the alert event is not greater than the threshold, the control unit may communicate the alert to "slow" clinicians C, F, and G before communicating the alert to any other clinician. On the other hand, if the severity is greater than the threshold, the control unit may instead communicate the alert to "quick" clinicians D, A, and E, alternatively or additionally to communicating the alert to clinicians B, C, F, and G. Other factors that the control unit may consider include the number of alerts each clinician has received during a previous time period, the distance of each clinician from the patient, and seniority of each clinician, as described hereinbelow. (As described hereinbelow, the control unit may compute a score for each clinician that takes into account multiple factors.)

In some applications, the control unit is configured to compute the historical alert-response times by first normalizing the "raw" response times to account for such factors as distance from the patient and fatigue. For example, even if a clinician responded slowly to a particular alert, the historical alert-response time of the clinician might not rise if the control unit determines that the clinician was on call for the previous 24 hours and is therefore likely to have been fatigued.

For some applications, in accounting for clinician performance, the performance indication functionality is configured to account for the number of alerts generated over a given time period, and/or a level of sensitivity of the alert-generation functionality of the patient monitoring systems.

In some applications, the central monitoring system 120 sends a message to each unit 10 to switch from day to night mode. In night mode system volumes may be preset differently and bed exit alerts may be set differently. For example, some clinical teams prefer to have all their systems activated to a bed exit active mode at night even for those patients who are not at a fall risk since it allows the clinician to know that that specific patient is awake at night. By approaching that patient at night the clinician may identify a patient who needs help without relying on him activating the nurse call button. In addition, this helps improve patient satisfaction which is a key quality measure for hospitals. Other parameters that may automatically change at night versus day or in general per the time in day include the volume settings, brightness settings, alert threshold settings, time between patient turns, and escalation protocols for alerts. In general, the scope of the present invention includes providing central monitoring system control unit that is configured to simultaneously change alert settings of the sensors associated with each of the patients that is associated with the central monitoring system, based on time of day.

For some applications, signal analysis functionality 128 of central monitoring system control unit 124 is configured to analyze a rate at which the alerts are generated, and, in response thereto, to determine that a setting of alert-generation-functionality 92 of the patient monitoring systems should be changed. In response thereto, the signal analysis functionality generates an output that is indicative of a recommended change to the alert-generation functionality setting, and/or automatically changes the alert-generation functionality setting. For some applications, the analysis of the rate at which alerts are generated is performed based upon an overall alert rate of all of the patient monitoring systems associated with the central monitoring system. For some applications, a global change is made (or recommended to be made) to the alert-generation functionality settings of all of the patient monitoring systems associated with the central monitoring system in response to the rate at which it is determined that the alerts are being generated.

For some applications, central monitoring system 120 continuously collects alert response time information and compares to historic or peer averages. If a change (for example, a deterioration) is detected, the system immediately highlights the change. It also correlates the change with other parameters that may affect response time such as the number of overall alerts, the number of patients on bed exit alert, the number of patients on patient turn alert, and the ratio of clinicians to patients. For some applications, in response to response time increasing versus historical values or peer averages by more than a threshold amount, for example by more than 25 percent, the central monitoring system evaluates the actual number of alerts generated in the time period. For some applications, if the actual number of alerts generated within the time period has increased, the system checks whether the actual percentage of patients with bed exit alert activated is higher than historic or peer average values or whether the sensitivity level distribution is higher than historic or peer comparisons. If so, the system indicates that information to the managers or the nurses in order for them to consider changing the settings of the alert-generation functionality of the patient monitoring systems, in order to avoid alarm fatigue. Alternatively, the system automatically changes the settings of the alert-generation functionality of the patient monitoring systems. If the response times increase without corresponding higher than expected alarm rates, then this information is relayed to managers, this information typically being of value to managers since it indicates that additional training for the team may be required.

Conversely, if better than expected response times are found as compared to historic or peer data, then the system may highlight that information to managers and clinicians as defined in order to allow positive reinforcement and recognition to be given to appropriate team members. For some applications, if the response times are better than predefined settings or better than historic performance the system indicates that information to the clinicians and suggests that settings of the alert-generation functionality of the patient monitoring systems should be changed (e.g., tighter thresholds can be used, or higher sensitivities for alerts such as bed exit can be used). Alternatively or additionally, if the overall alarm rate for a group of patients or a hospital unit is below a defined threshold, the system suggests to a manager that settings of the alert-generation functionality of the patient monitoring systems should be changed (e.g., tighter thresholds can be used, or higher sensitivities for alerts such as bed exit can be used). Alternatively, the system automatically changes the settings of the alert-generation functionality of the patient monitoring systems.

In the above-described manner, clinicians are able to adapt the sensitivity level of the patient monitoring systems in a hospital department to be optimized to a level of alarms that on the one hand minimizes alarm fatigue, and on the other hand maximizes patient safety. For example, some hospitals believe that nurses should not receive more than 2 alarms per nurse per hour. If over a period of time of 4 hours, for example, the alarm rate that is counted and analyzed by a central server is lower than 1 alarm per nurse per hour the system indicates that information to clinical managers, indicating that higher sensitivities or tighter thresholds can be used for alerts such as bed exit or respiratory rate respectively. Alternatively, these changed settings can be activated automatically upon detection of the low overall alarm rate. For example, if over the previous 4 hours, the central monitoring system detects that the overall per nurse alarm rate is lower than 1 alarm per nurse per hour, the system automatically tightens all thresholds by 10 percent and increases the bed exit sensitivities for those patients who are on bed exit alarm to one higher level. Conversely if the alarm rate is 3 alerts per nurse per hour, the system indicates to a clinical manager that the alarm thresholds and sensitivities should be changed to reduce overall alarm rate in order to manage alarm fatigue. Alternatively, these changed settings can be activated automatically upon detection of the high overall alarm rate.

Similarly, even without response time analysis, in some applications, the central monitoring system analyzes the distribution of patients on bed exit alerts, patient turn alerts or respiratory and cardiac alerts, and the distribution of sensitivities and thresholds. If the distribution differs from historic or peer averages or from preset guidelines this information is indicated to clinicians or managers. This helps identify cases where possible sub-optimal alert-generation settings are being used for the system.

Reference is again made to FIG. 5. For some applications, a location-sensing system is used with patient monitoring systems 10 and central monitoring system 120. Typically the location-sensing system includes a plurality of location sensors 132 that are associated with respective resting surfaces (e.g., bed, or chairs upon which patients rest), patients, displays, and/or clinicians (e.g., nurses or doctors). For example, nurses and patients may be equipped with automatic identification devices utilizing technologies such as RFID or barcode, the identification devices acting as location sensors 132. This allows system 10 to automatically identify that a nurse has approached a patient when an alert has been activated and which nurse it is. In addition, it allows system 10 to automatically identify when a patient has moved from a chair to a bed, or vice versa, or when the patient was moved from one bed or chair to another. This helps save the clinician time and reduces the possible errors in inputting such information manually into the system.

In some applications, in response to the location-sensing system signal, the signal analysis functionality of a local patient monitoring system, or of the central monitoring system, formats the display of data on the display associated with the patient monitoring system or with the central monitoring system in a given format. For example, the signal analysis functionality of a local patient monitoring system may automatically identify that a clinician such as a physician, nurse, nursing manager, or nurse assistant is approaching the bedside of patient 1. This is done in some cases utilizing an RFID technology badge worn by the clinician, the badge being part of the location-sensing system. The signal analysis functionality receives a location-sensing system signal, which may include an indication of the location of the patient monitoring system of patient 1, and the location of the clinician. Alternatively, the location sensing system may include a proximity sensor that detects the clinician is in the vicinity of the patient monitoring system without knowing the absolute location of the clinician and/or its own absolute location but can calculate the distance or relative position of the clinician to the display based on the proximity sensor. When the signal analysis functionality identifies that the clinician is in close proximity to the display, the system automatically adapts its user interface based the specific identity of the clinician in its vicinity. For example, in response thereto, one or more of the following functionalities may be implemented:

- User interface 24 of the individual patient monitoring systems may be a touch screen display, which acts as an interface for controlling parameters of the system. The default configuration of the touch screen display may be that it is locked for certain changes (e.g. changing thresholds of respiratory alerts). For some applications, the touch screen display is automatically unlocked when a clinician who has appropriate privileges approaches the system. For example, in some institutions, a nurse may be allowed to change parameters relating to fall prevention alarms but not parameters related to respiratory alarms, while a physician may be allowed to change both types of settings, so the display will only unlock the fall prevention parameters when a nurse is in its vicinity and will unlock all alarm setting functionality when a physician is close by.
- The data displayed may be adapted according to predefined or previously requested data relevant for the clinician who is currently next to the monitor. For example, a physician may be shown the detailed waveform of respiration or cardiac parameters, while a nurse may be shown a tabular display of the most recent alerts, and a nurse assistant who is in charge of turning a patient for pressure ulcer prevention may be shown the last time that the patient was turned, or similarly the last time the patient was taken to the bathroom.
- A clinician who is approaching this patient for the first time may be shown detailed historical information, while a nurse who visited the patient within the previous one hour is shown a more focused display of only the parameters that changed during that last hour.

If two nurses approach the patient simultaneously and the system has access to the database of the nurse shift assignments and one of the nurses belongs to a previous shift and one to the current shift, the system identifies that this is a shift change handoff process and displays the relevant information from the previous shift that the previous shift nurse should share with the oncoming new shift nurse in order to make sure that data is transferred between the clinicians in an effective and efficient manner.

The display, which is usually turned off in order not to confuse the patient or not to disturb the patient's sleep, may be turned on when the clinician enters the room.

In a hospital that has a rounding protocol wherein the nurses need to visit the patient every defined interval of time (e.g., every 2 hours) and the nurse enters the room after this amount of time elapsed since the previous visit to the room, the display reminds the nurse that he should go through the defined rounding steps (e.g. ask the patient if he is comfortable, and if he needs to go to the bathroom). The system then resets a time counter until the next rounding visit is required and logs that a rounding visit took place.

For some applications user interface 122 of central monitoring system 120 includes a display that shows the ongoing clinical information of a large number of patients. The central monitoring system may also store information regarding which patients are assigned to which clinician. For example, on a standard surgical floor, five patients are assigned to each nurse. Large screen displays that show the ongoing patient information of all patients on the floor are placed in the corridors of the floor. For some applications, when a nurse walks by the large screen display, the location system identifies that this specific nurse is close to the display and highlights the information pertaining to the patients that are assigned to that nurse. In this way the nurse can efficiently glance at the patients assigned to him without being distracted by less relevant information of other nurses' patients. Additionally, when the nurse walks by the large screen display, the system may calculate the direction in which the nurse is moving and highlights information pertinent to patients that are in the direction the nurse is walking. Alternatively, if an alert event exists for a patient assigned to the nurse, and the patient is not located in the direction in which the nurse is walking, then an indication is displayed that indicates that the nurse should walk in the opposite direction. Alternatively if the clinician is moving faster than a defined speed the display is not adjusted at all or is adjusted to show relevant information at larger fonts than usual in order to facilitate reading during fast pace walking.

Reference is again made to FIG. 5. In some applications, one of the local patient monitoring systems 10 determines that an alert event that requires immediate attention has occurred. For example, the system may determine that a patient who is not allowed to leave his bed on his own due to fall risk is leaving his bed, or the system may identify that a cardiac arrest has occurred. For some applications, signal analysis functionality 128 of the central monitoring system control unit determines a subset of clinicians to whom to communicate the alert, in response to the location-sensing system signal, e.g., in response to signals from locations sensors 132 that are associated with respective clinicians, and/or a location sensor associated with a resting surface (e.g., a bed) upon which the patient is lying. For example, the system may communicate the alert, with information regarding the location of the patient at risk, to the nearest relevant clinician or clinicians (e.g. nurse or nurse assistant) to the patient. The communication of the alert to the clinician is done, for example, via a pager the clinician is carrying. The nearest clinician is determined by the processing unit based on the information of the location of clinicians and the location of the monitored patient. The system then monitors the location of the alerted clinician, as indicated by the location-sensing system signal. (For example, the system may monitor how quickly the clinician starts moving in the direction of the patient at risk.) If no movement by the alerted clinician is identified within a defined length of time (for example, 10 seconds), and/or if the alerted clinician is not within a given distance of the patient within a given time period of the alert, a second alert is communicated, i.e., the clinician is notified again, and/or one or more additional clinicians (e.g., more senior clinicians, and/or managers) are alerted as well. If the first alert is communicated to more than one clinician, the control unit may communicate the second alert in response to fewer than a given number of the alerted clinicians being within a given distance of the patient, and/or fewer than a given number of the alerted clinicians moving toward the patient. For example, if none of the alerted clinicians is within the given distance, and/or none of the alerted clinicians is moving toward the patient, the control unit may communicate the second alert.

For some applications, the identities of clinicians to whom the alert was communicated and who did not respond to the alert within the defined length of time are communicated to a more senior clinician, and/or a manager. In general, for some applications, information regarding clinician response times (e.g., the time it takes the clinician to start moving in the direction of the alerting patient, and the time it takes the clinician to reach the patient location) is logged and reported to managers for quality improvement purposes. Clinicians can be rewarded based on their speed of response to alerts and the number of alerts they respond to in time. In addition, after the immediate alert, in some applications the system has the ability to accept input on whether the outcome of this alert was positive (i.e. was the patient fall prevented or was the patient under cardiac arrest saved). That information is analyzed and reported together with the clinician response profile in order to identify correlation between clinician performance and outcomes and use that for team training, e.g., to provide positive reinforcement when outcomes are positive, and provide appropriate managerial intervention when improvement is required.

For some applications, in response to an alert event having occurred, signal analysis functionality 128 of the central monitoring system control unit determines a subset of clinicians to whom to communicate an alert, in response to the location-sensing system signal, in addition to one or more additional factors. For example, the alert may be categorized (e.g., into a bed exit alert, a heart rate threshold alert, a respiratory rate threshold alert, a heart rate trend alert, a respiratory rate trend alert, or loss of vital signs alert), and the signal analysis functionality may determine the subset of clinicians to whom to communicate an alert, in response to both the location-sensing system signal and the categorization of the alert. Alternatively or additionally, the signal analysis functionality may determine the subset of clinicians to whom to communicate the alert based at least in part on the number of alerts that respective clinicians have received within a previous given time period, and/or based upon a level of seniority of respective clinicians. For example, the control unit may compare respective numbers of alerts that the clinicians have received within a previous given time period (e.g., the previous 24 hours), and in response to the comparison, the control unit may communicate the alert to a subset of the clinicians before communicating the alert to any other clinician.

Typically, in response to the comparison, the control unit communicates the alert to clinicians who have received a lower number of alerts during the previous given time period, relative to other clinicians, thus allowing the other, potentially overworked and/or alarm-fatigued clinicians to rest. For example, the control unit may be configured such that a likelihood that the control unit will include a given clinician in the subset of clinicians is a decreasing function of the number of alerts received by the given clinician within the previous time period. Alternatively or additionally, the control unit may communicate the alert to the subset of the plurality of clinicians in response to each clinician belonging to the subset having received a lower number of alerts during the previous time period than at least one clinician who does not belong to the subset. For example, the table below shows a scenario in which a number of clinicians have received different numbers of alerts during a previous time period.

TABLE 2

| Clinician | Number of Alerts |
|---|---|
| A | 5 |
| B | 7 |
| C | 2 |
| D | 3 |
| E | 5 |
| F | 1 |
| G | 8 |

The control unit may order the clinicians by number of alerts received, and select the subset in response thereto. For the scenario above, the ordering (in increasing order) is F, C, D, A, E, B, and G. The control unit may communicate the alert to (for example) clinicians F, C, and D before communicating the alert to any other clinicians (even if one of the other clinicians is more skilled than clinicians F, C, and D), since clinicians F, C, and D are less likely to be overworked and/or alarm-fatigued than the other clinicians.

Typically, the control unit is configured to determine whether the alert has been responded to, and, in response to the alert not having been responded to within a given period of time (e.g., 5-10 minutes), to communicate the alert to a clinician not in the subset of the plurality of clinicians. For example, for the scenario described above, the control unit may communicate the alert to clinicians A and E, in response to none of clinicians F, C, and D responding within the given period of time. In some applications, in response to the subset not responding within the given period of time, the control unit communicates the alert to a more senior clinician than the clinicians in the subset. For example, the control unit may communicate the alert to clinician G, even though clinician G received the greatest number of alerts during the previous time period, if clinician G is senior to clinicians F, C, and D. In some applications, the control unit communicates to the more senior clinician identities of the clinicians in the first subset of the clinicians.

In some applications, as described hereinabove, the location sensing system identifies respective locations of the plurality of clinicians, and generates a location-sensing-system signal in response thereto. In such applications, the control unit may designate the subset of clinicians further in response to the location-sensing-system signal. For example, in response to the respective locations of the clinicians (as indicated by the location-sensing-system signal), the control unit may calculate respective estimated times for the clinicians to reach the patient, and designate the subset of the plurality of clinicians in response to the estimated times. For example, the table below shows a scenario in which the clinicians have different respective estimated times. (The first two columns of the table below are identical to Table 2.)

TABLE 3

| Clinician | Number of Alerts | Estimated Time to Reach Patient (AU) | Score |
|---|---|---|---|
| A | 5 | 4 | 4.7 |
| B | 7 | 2 | 5.3 |
| C | 2 | 5 | 3 |
| D | 3 | 8 | 4.7 |
| E | 5 | 3 | 4.3 |
| F | 1 | 20 | 7.3 |
| G | 8 | 7 | 7.7 |

The control unit may order the clinicians by a function that takes into account both the number of alerts and the estimated times. For example, the control unit may compute a score for each clinician that gives a relative weighting to each of the two quantities. These scores are shown in the final column of Table 2, using the purely illustrative formula $\frac{2}{3}*N+\frac{1}{3}*T$, where N is the number of alerts and T is the estimated time to reach the patient. Using these scores, the ordering of the clinicians would be C, E, A, D, B, F, and G. The control unit may then, for example, identify the subset consisting of clinicians C, E, and A. This subset is typically different from the subset that would have been selected had the control unit considered only the number of alerts, or only the locations of the clinicians.

Typically, the estimated times are computed by taking into account the respective walking distances of the clinicians from the patient. In other words, the control unit takes into account the location of each clinician and the layout of the hospital corridors, such that the estimated time for a particular clinician reflects the distance that the clinician would need to travel to reach the patient. Furthermore, the control unit may also calculate the respective estimated times in response to times that were historically required to traverse portions of the hospital. For example, in calculating the estimated times, the control unit may take into account historical averages, such as the average historical time needed to traverse a particular corridor or travel between floors in a particular elevator. In some applications, the control unit calculates the estimated times in response to the current positions of any relevant elevators; for example, a greater expected time will be calculated for a particular clinician if the elevator is not near the clinician's current floor, relative to if the elevator were near the clinician's current floor. In general, the historical averages, and/or other data used by the control unit to calculate the estimated times, may be stored in computer memory, e.g., in a relational database. For example, a relational database may be used to store a weighted graph that represents the historical average times to travel between various locations in the hospital.

Typically, the control unit determines a severity of the alert event. If the severity is less than a threshold, the control unit generally behaves as described above, i.e., the control unit communicates the alert to the subset of clinicians before communicating the alert to any other clinician. However, if the severity is not less than the threshold, the control unit communicates the alert to a group of the clinicians that is larger than the subset. For example, in the scenario described with respect to Table 3, the control unit may limit the alert to clinicians C, E, and A only if the severity of the alert is less than a threshold; otherwise, the control unit may communicate the alert to (for example) all of the clinicians within a distance of 6 (arbitrary units) from the patient, i.e., clinicians C, E, A, D, and B. (If the alert event is sufficiently severe, the control unit may communicate the alert to all relevant clinicians, regardless of their respective distances from the patient.)

For some applications, the pattern analysis generates a score for each of the clinicians based upon the location-sensing-system signal in addition to the category of the alert event, the number of alerts that respective clinicians have received within a previous given time period, and/or a level of seniority of respective clinicians. The signal analysis functionality determines to whom to communicate the alert based upon the scores of the respective clinicians. For example, the score may be calculated based upon the following formula:

$$S = k1*D + k2*N + k3*SN + k4*F$$

where:
k1, k2, k3, and k4 are respective weighting factors;
D is distance of the clinician to the location of the patient;
N is number of alerts the clinician received to date;
SN is number of years clinician is working in the institution, or in his/her current position; and
F is a fitness parameter that may be based on a database that provides a fitness for each type of clinician (e.g., each level of seniority of the clinicians) in dealing with each type of alert.

By way of example, the fitness parameters may be in accordance with the following table:

TABLE 4

| | Assistant Nurse | Nurse | Nurse Manager | Physician |
|---|---|---|---|---|
| Bed exit alert | 0 | 5 | 10 | 100 |
| Heart rate threshold alert | 20 | 0 | 5 | 30 |
| Respiratory rate threshold alert | 20 | 0 | 5 | 30 |
| Heart rate trend alert | 100 | 5 | 0 | 10 |
| Respiratory rate trend alert | 100 | 5 | 0 | 10 |
| All vital signs signal lost | 0 | 0 | 0 | 0 |

For some applications, the formula that is used to calculate the scores for respective clinicians varies depending on whether the signal analysis functionality is determining to whom to send an initial alert, to whom to send a reminder alert, and/or depending on the number of repeated alerts that have been generated for the patient within a previous given time period. For example, a reminder alert may be communicated to a manager, in addition to a nurse or a doctor. Alternatively or additionally, the third heart rate alert within an hour may be immediately directed to a physician as opposed to a nurse.

For some applications, each patient is generally assigned to a set of clinicians, and the signal analysis functionality determines to whom to communicate the alert based upon the location-sensing-system signal in addition to which clinicians are generally assigned to the patient. For example, the signal analysis functionality may initially only communicate the alert to clinicians who are assigned to the patient. If none of the clinicians who are assigned to the patient responds to the alert within a given time period, the signal analysis functionality may then communicate the alert even to clinicians who are not assigned to the patient.

Reference is again made to FIG. 5. In some applications, at least some of the local patient monitoring systems 10 are mobile and utilize location sensors 132 (e.g., an RFID type location device) in order to communicate their locations to central monitoring system 120. Typically the location sensor communicates the location of the resting surface (e.g., the bed, chair, wheelchair, or stretcher) associated with the patient monitoring system that is generating the alert. For some applications, this is used to augment or replace the information about the patient identification. Thus, for example, an application of the system monitors patients in beds that are moved from one location to another, patients sitting in bedside chairs, in wheelchairs, or in ER waiting room seats. For such applications, system 10 is intended to be mobile and to alert the clinician upon a change in patient condition that requires intervention. For example, if the patient is trying to get out of bed without assistance when he is not supposed to, or if the patient has a significant change in heart rate or respiratory rate, system 10 communicates the nature of the alert to the central monitoring system which presents that information to the relevant nurse or physician. The central station simultaneously presents the location of system 10 generating the alerts.

In accordance with respective applications, the location information is communicated to central monitoring system 120 from system 10, or read by the central monitoring system from an asset tracking type system utilizing technology such as RFID that provides a unique identifier to system 10. Thus, the clinician can be given immediate actionable information on the type of alert as well as the exact location of the patient that requires intervention. This information can be communicated to the clinician at the central monitoring system or from the central monitoring system to a mobile device the clinician carries.

For some applications, the above process is performed without requiring the identification of the patient to be known to the system. For example, in an ER waiting room, patient turnaround is extremely high. Patients may stay for only a few minutes in a waiting room chair or stretcher. A nurse who wants to monitor a patient for vital signs, motion, bed exit, or chair exit may not have enough time to enter patient identification information for every new patient coming in. Similarly, patients in wheel chairs that are used to move patients around in the hospital may spend very short time periods in the wheel chairs and the nurses may not have the opportunity to enter patient identification information for every new patient using the wheel chair. In such cases, the system alerting based on the location of the resting surface (e.g., the bed, chair, wheelchair, or stretcher) associated with the patient monitoring system that is generating the alert can allow the clinician to intervene despite the fact the patient's identification is not known to the system. The central monitoring system will typically display to the clinician the type of alert and the location of the patient requiring the alert without the patient identification information. In some applications, the sensor is fixed in location for example in specific chairs in an ER waiting room and the patients are sent to specific locations as per the required functionality. For example, a subset of specially colored chairs in the ER waiting room may be used to monitor patients who are at risk of falling, and another subset of chairs with a different color may be used to monitor only cardiac activity. By sending a patient to a specific chair without having to wire the patient to anything and without having to enter patient identification into the system, a nurse can activate specific monitoring and alerting functionality without any setup work being required by the nurse or the patient.

In some applications, system 10 has a time counter running while the patient is in bed. Every predefined period of time (e.g., at a predefined time of between 30 minutes and 5 hours, e.g., two hours), the system sends a reminder to a nurse to check on the patient. The reminder is displayed at user interface 122 of central monitoring system 120, as well as being communicated to a mobile device carried by the nurse. When the nurse enters the room, the nurse interacts with local patient monitoring system 10, in order to indicate that he has checked on the patient. For some applications, the local monitoring system presents to the nurse in the room questions that require answering, or reminders regarding things that the nurse should check. For example: "is the patient in pain?" or "does the patient need to go to the bathroom?" In some applications, the nurse enters the response to these questions into user interface 24 of system 10. The information regarding nurses' response time, and answers to questions to these reminders is logged and formatted in reports made available to managers as part of performance data that enables effective management of the clinical team.

The aforementioned reports may show, for example, average performance as well as personal performance of each nurse, as well as trending in performance over time and as compared to other hospital departments, other hospitals, regional averages and/or targets set by management. In some applications, system 10 helps support a hospital policy to take the patient proactively to the bathroom every preset amount of time, for example every 4 hours. This is useful in preventing the patient from trying to get out of bed on his own which may create a risk of falling. System 10 has a time counter while the patient is in bed. The nurse receives a reminder via central monitoring system 120, or via a mobile device (e.g., a pager) to visit the patient every set amount of time and take that patient to the bathroom. When the nurse acknowledges the alert at the bedside on user interface 24 of system 10, system 10 provides a reminder to the nurse to take the patient to the bathroom. Then, system 10 actually detects whether the patient has exited the bed and logs that information. In some applications, if a bed exit is not detected, the reminder is sent again to the nurse and possibly escalated to other nurses or to a manager. In another application, if bed exit is not detected, it is logged and presented in reports made available to managers and forms part of the performance data mentioned hereinabove. In a similar manner, for some applications, timers are set and bed exit is detected by a sensor for a patient in a chair and reminders are sent to the nurse. In some applications, system 10 automatically resets the timing counter if the patient has left the bed or the chair prior to the preset time limit. In some applications, system 10 detects when the patient is sleeping and/or when the patient's movement level is below a threshold and if the timing counter reaches the set threshold when the patient is sleeping, a reminder to take the patient out of bed is not sent to the nurse. The alert is postponed until system 10 detects that the patient has woken up, or until the detected movement level has crossed a threshold level of movement amplitude, or number of movements per time period, the detected movement level indicating that the patient has woken up. Once the detected level of movement has crossed the threshold, or patient awakening is detected, the postponed reminder is immediately sent to the nurse.

In some applications of the present invention, system 10 notifies the nursing care staff of any of the alarm conditions described herein using the existing nurse call system used in the healthcare facility. In some applications of the present invention, system 10 persistently reminds nurses of a continued deterioration in the condition of a patient until intervention is successful.

Reference is again made to FIG. 5. In some applications of the present invention, system 10 is integrated into a communication system wherein information for multiple systems 10 is accumulated and presented at central monitoring system 120 that is located, for example, in the hospital's nurse station. For some applications, local patient monitoring systems are located in respective patients' homes and central monitoring system 120 is located at a call center. In such environments, there are often multiple nurses each assigned to take care of a group of one or more patients within the unit or region. It is useful to allow grouping patients assigned to a specific nurse in a convenient, easy to view way that can be understood with a quick glimpse as a clinician walks by a display. In some applications, each nurse is assigned a color at the beginning of his shift. All patients assigned to that nurse are then automatically or manually assigned to the same color. That information is entered into the central display station through an input means (for example, utilizing a keyboard or touchscreen), or received automatically (for example, from a hospital's computerized ADT (Admit Discharge Transfer) system). The central display groups patients by their color coding, so the nurse can view his group while walking by the display and easily see whether any of his patients require immediate attention. Furthermore, in some applications, the nurse also gets assigned a mobile phone or pager for his shift. This phone is marked with the same color assigned to the nurse, and accordingly the nurse gets the alerts related only to the patients assigned to that nurse. In some applications, the vital signs information about each patient can be presented in matrix form, so each column may represent a different nurse.

For some applications, system 10 is utilized to monitor ventilated patients, for example, as described in US 2008/0275349 to Halperin et al. (now abandoned), which is incorporated herein by reference. System 10 utilizes a sensor under the patient's mattress, which is optionally contactless, in order to continuously monitor the mechanical motion signal of a ventilated patient and, upon detecting a change in the motion signal, to alter the ventilation status of the patient, e.g., by changing the physical position of the ventilation tube, taking out the tube, and/or changing the ventilation system parameters.

For some applications, system 10 includes a piezoelectric sensor installed on a semi-rigid plate which is placed on the bed frame under the mattress, to monitor the patient's breathing and heart parameters, as described hereinabove. The plate is installed in the top section of the bed where usually the patient's head and chest are located. The sensor plate also has an accelerometer installed thereon, to facilitate measurement of the tilt angle of the plate.

In many beds, the top section of the bed may optionally be angled upwardly. In general, orienting the top section of the bed at an angle that is greater than a given angle with respect to a lower section of the bed has been shown in clinical trials to be helpful in preventing various respiratory diseases, and in helping patients who have respiratory diseases to recuperate faster. Specifically, for patients who are ventilated, some clinical work has shown that orienting the top section of the bed at an angle that is greater than 30 degrees (e.g., greater than 45 degrees) with respect to a lower section of the bed significantly reduces the incidence of ventilator-associated pneumonia, which is a significant concern for ventilated patients.

For some applications, system 10 continuously logs, and optionally displays, the angle of the top section of the bed, as detected by the accelerometer. For some applications, system 10 generates an alert if the angle is below a set threshold (e.g. 30 degrees), or alternatively if an angle below that threshold has been maintained for a time period that is greater than a given threshold (e.g., if the angle has been set at an angle smaller than 30 degrees for more than 8 consecutive hours, or if the angle has been below 30 degrees for more than 12 hours during the last 24 hour period).

For some applications, in order to prevent unnecessary alerts and reduce clinician alarm fatigue, system 10 uses the respiratory or cardiac related motion detected through the piezoelectric sensor in order to identify that a patient is in bed, and the timer that counts the amount of time the patient is at a low angle is only activated if the patient is actually in bed.

For some applications, the piezoelectric sensor is used to detect when a patient is on a ventilator by identifying a characteristic of a signal that is generated in response to a parameter of the patient when a ventilator is active. For example, when a ventilator is active, the variability of the breathing motion signal between consecutive breaths is significantly smaller than with non-ventilator assisted breaths or when the ventilator is not active. Therefore, a variability of the breathing motion signal between consecutive breaths may be detected in order to detect when the ventilator is active. Alternatively, a signal having a frequency that is the frequency at which electricity is provided (e.g., 50 or 60 Hz) may be detected in order to detect when the ventilator is active. Alternatively, an additional vibration sensor may be placed on the ventilator itself, or a digital communication signal may be received from the ventilator into system 10 to indicate that the ventilator has been activated. For some applications, the system continuously logs, and optionally displays, the activation times of the ventilator, as well as the head-of-bed angle. Alternatively or additionally, if the angle of the top section of the bed is below a threshold angle (e.g. 45 degrees) for an extended period of time, or for more than a threshold percentage of the time that the patient is on an active ventilator, an alert is generated. For some applications, the angle of the top section of the bed and the ventilation information are continuously displayed for effective management purposes of the nursing staff.

Figure 6:
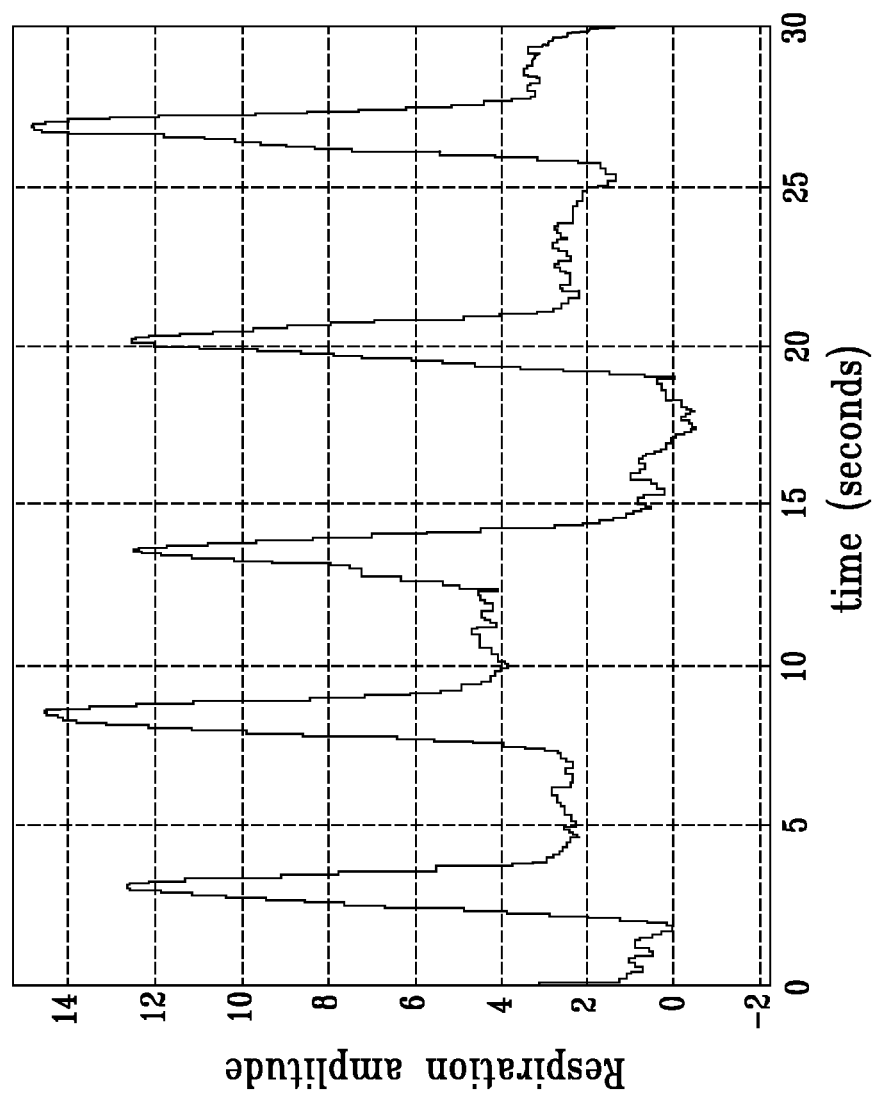
FIG. 6 is a graph showing a respiratory signal measured on a ventilated patient when the patient was ready to be weaned off the ventilation system, in accordance with some applications of the present invention.
Figure 7:
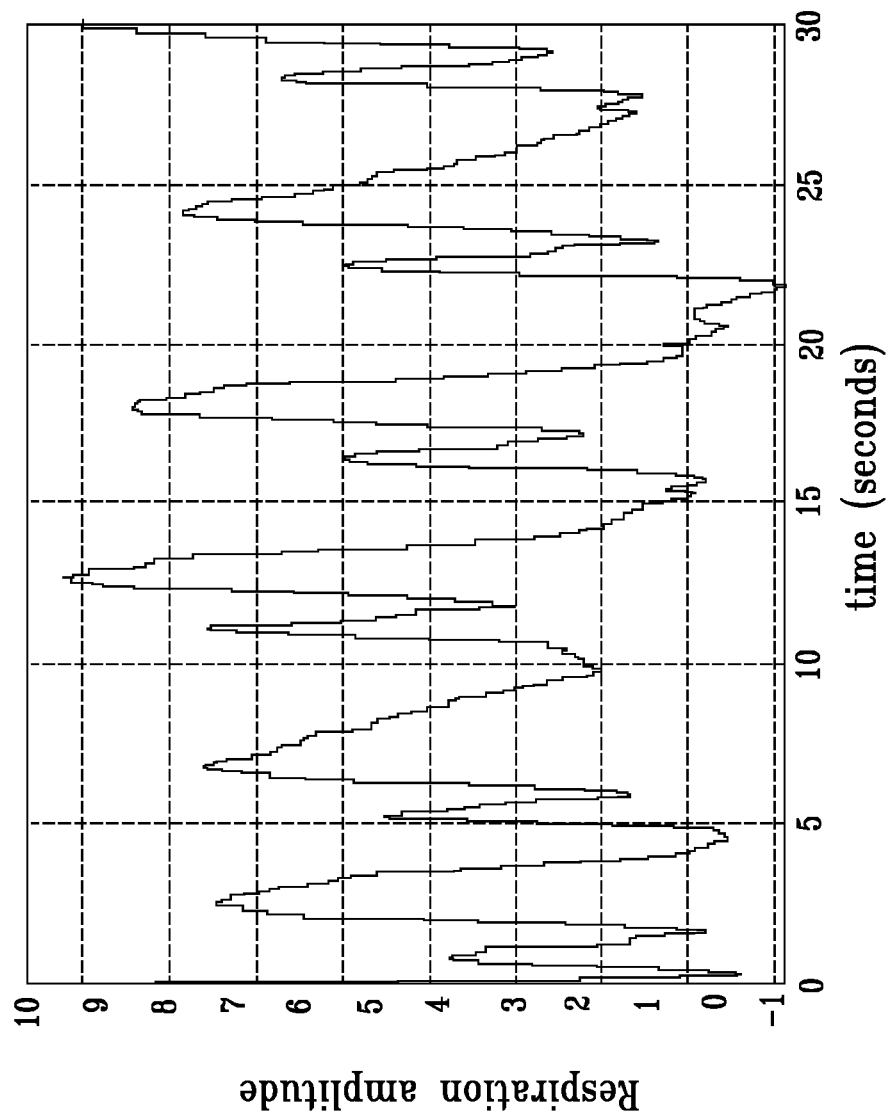
FIG. 7 is a graph showing a respiratory signal measured on a ventilated patient when the patient was not yet ready to be weaned off the ventilation system, in accordance with some applications of the present invention.

Reference is now made to FIGS. 6-8. FIG. 6 is a graph showing the respiratory signal measured on a ventilated patient when the patient was ready to be weaned off the ventilation system, in accordance with some applications of the present invention. FIG. 7 is a graph showing the respiratory signal measured on a ventilated patient when the patient was not yet ready to be weaned off the ventilation system, in accordance with some applications of the present invention. FIG. 8 is a graph showing the respiratory signal measured on a ventilated patient who had to undergo a tracheostomy, in accordance with some applications of the present invention.

For some applications, pattern analysis module 16 (e.g., breathing pattern analysis module 22 of the pattern analysis module) analyzes the motion sensor signal, to distinguish between respiratory motion of the patient that is caused by autonomous breathing activity and respiratory motion of the ventilated patient caused by the ventilator. In response thereto, the pattern analysis module determines whether the patient is ready to be weaned off the ventilator, and generates an output that is indicative of whether the patient is ready to be weaned off the ventilator.

As the patient condition improves, system 10 detects a trend towards normal breathing patterns that may be an indication for the clinician that the patient is ready to be weaned off the mechanical ventilator. In some applications, sensor 30 detects the combined mechanical motion signal generated by both the autonomous movement of the patient and the motion caused by the ventilator impact on the body. The combined signal is analyzed by pattern analysis module 16 (e.g., by breathing pattern analysis module 22 of the pattern analysis module) and when the two signals conflict with each other as shown in FIGS. 8-9, a double-peaked respiratory signal is detected. Typically, in response to detecting a double-peaked signal (or another respiratory signal that indicates that the patient is not ready to be weaned off the ventilator) an output is generated that indicates that the patient is not ready to be weaned off the ventilator. However, when the autonomous breathing signal strengthens and is well correlated with the ventilator motion the correlation of the two signals is detected as a single peaked smooth respiratory signal, e.g., as shown in FIG. 7. Therefore, in response to detecting a single-peaked smooth respiratory signal (or another respiratory signal that indicates that the patient may be ready to be weaned off the ventilator) an output is generated that indicates that the patient is ready to be weaned off the ventilator. In some applications, the use of auxiliary muscles is detected and used as an indication that the patient is not ready for weaning. In some applications, the ratio of expiration to inspiration, and/or the duty cycle of the respiration motion as part of the respiratory cycle is used as an indication of readiness by the patient for weaning. A duty cycle below a threshold may indicate that the patient breath is gaspy and the patient is not ready for weaning. For some applications, a double-peaked respiration signal is detected using techniques described in US 2011/0046498 to Klap (issued as U.S. Pat. No. 8,585,607), which is incorporated herein by reference.

For some applications, pattern analysis module 16 of system 10 (e.g., breathing pattern analysis module 22 of the pattern analysis module) detects that a ventilated patient currently getting a relatively minor assistance from the ventilator (for example, pressure support ventilation, via a ventilator operating in "PSV mode") is not ready for extubation (i.e., is not ready to be weaned off the ventilator). Alternatively or additionally, the system is used for detecting that a patient who was recently extubated may require re-intubation or other respiratory treatment to prevent re-intubation. In response thereto, the pattern analysis module generates an output indicating that the patient is not ready to be weaned off the ventilator, or indicating that the patient may require further respiratory therapy. In some applications, this detection is done by identifying an unstable respiration pattern. For example, the pattern analysis module may identify an unstable respiration motion pattern (e.g., an unstable respiration amplitude pattern) in a signal generated by sensor 30, the signal being indicative of both respiration motion and a cardio-ballistic-effect related motion. An unstable respiration amplitude pattern can be detected in several ways. For example, pattern analysis module 16 may detect an unstable respiration pattern by detecting one or more of the following patterns:

High amplitude respiration cycles (significantly higher than neighboring cycles) that appear relatively frequently (about every 30 seconds to 120 seconds);

Apneas for 20 seconds or more; and/or

A generally unorganized respiration signal that does not follow a standard cyclical pattern.

It is noted that for some applications, the pattern analysis module (e.g., breathing pattern analysis module 22 of the pattern analysis module) generates an output indicating that the patient may require respiratory therapy in response to identifying a non-apnea unstable respiratory signal.

For some applications, the pattern analysis module 16 (e.g., breathing pattern analysis module 22 of the pattern analysis module) detects an unstable respiration pattern by utilizing the following signal analysis steps:

4. A respiration related motion signal and a cardiac related motion signal are filtered from the mechanical sensor signal that is detected by sensor 30.
5. A sliding window of 10 to 60 seconds (for example 20 seconds) is used to estimate the current normalized respiration amplitude every 10 to 60 seconds (for example 20 seconds).

The normalized respiration amplitude is measured in reference to heart pulse amplitude (for example, if the filtered respiration signal amplitude is 6000 and the filtered heart pulse signal amplitude is 1000—the normalized respiration amplitude is 6)

6. The absolute difference in the normalized respiration amplitude between successive time windows is calculated and compared to a threshold, for example 0.85. If that difference is higher than the threshold, then the respiration at this window is marked as unstable.

For some applications, pattern analysis module (e.g., breathing pattern analysis module 22 of the pattern analysis module) generates an output such as to indicate to a clinician that the patient has an unstable respiration pattern if, within a period of several hours to several days (for example, one day), the accumulative duration of time windows that are marked as unstable exceeds by a threshold factor (for example, a factor of 1.85) the accumulative duration of time windows that are not marked as unstable. For some applications, in response thereto, the pattern analysis module generates an output such as to indicate to a clinician that the patient may not be ready for weaning, or, if the patient has been weaned already, that he may require re-intubation or other form of respiratory therapy or assistance.

Reference is again made to FIG. 4. For some applications, pattern analysis module 16 of patient monitoring system 10 includes shallow-breathing-pattern identification functionality 101 that is configured to detect a situation in which the patient's breathing pattern is shallow. Fast and/or shallow respiration may indicate poor pulmonary function. For example RSBI (Rapid shallow breathing index), is used as a criterion for ventilation weaning in hospitalized patients. In some applications of the present invention, system 10 identifies rapid shallow breaths by identifying an increase in respiration rate with a decrease in respiration motion signal size and without a change in patient's posture compared to before the onset of shallow breathing. In some applications of the present invention, system 10 identifies rapid shallow breathing by identifying a decrease in magnitude of respiratory sinus arrhythmia of the patient.

For some applications, shallow-breathing-pattern identification functionality 101 of system 10 analyzes the sensor signal of sensor 30 (which is typically a mechanical sensor placed under the patient's mattress) in order to identify whether a respiration signal is abnormally shallow, and, in response thereto, the system identifies that the patient is undergoing poor pulmonary function, and/or generates an alert. For some applications, the respiration rate measured by system 10 is combined with the shallow breath indication, and, in response thereto, the system identifies that the patient is undergoing poor pulmonary function, and/or generates an alert. Alternatively, the poor pulmonary function is identified based upon identification of shallow respiration, regardless of the patient's respiration rate.

For some applications, the identification of shallow respiration signal is performed by identifying that the strength of the heart rate related signal implies that the patient is located directly above the sensor. In such a case, the strength of the respiration related signal is expected to be within a known range as compared to the heart rate related signal energy level. For example, the strength of the respiration related signal level may be expected to exceed the strength of the heart rate related signal level by a factor of more than 2. If the ratio of the strength of the respiration related signal to that of the heart rate related signal is below the expected threshold, system 10 indicates that the patient's respiration is abnormally shallow. Alternatively, if the ratio of the heart rate related signal to that of the strength of the respiration related signal is above an expected threshold (e.g., 0.5), system 10 indicates that the patient's respiration is abnormally shallow. In general, if the ratio of the strength of the respiration related signal to that of the heart rate related signal is below an expected threshold, system 10 may interpret this as indicating that the patient's respiration is abnormally shallow, regardless of the strength of the heart rate related signal.

Figure 9B:
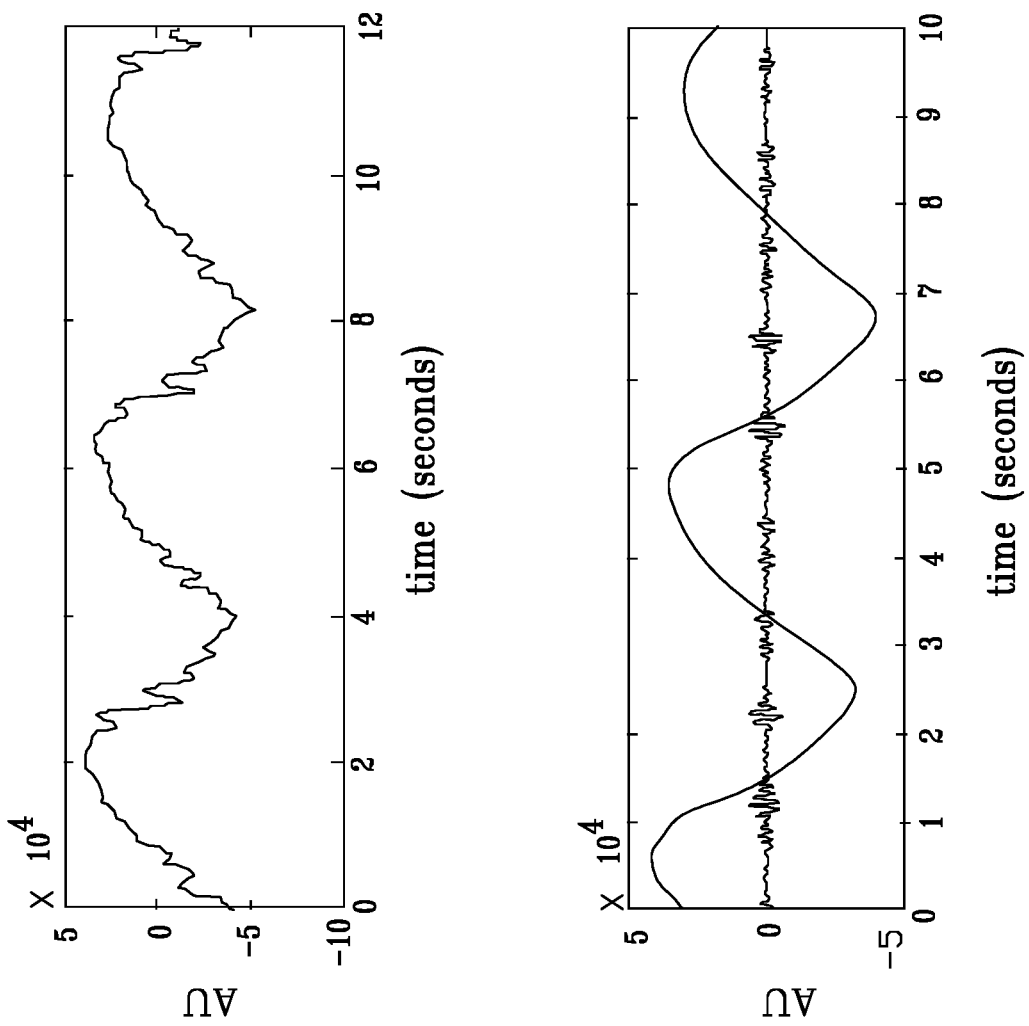

Reference is now made to FIGS. 9A-B, which are sets of graphs showing signals of, respectively, a patient undergoing normal breathing and a patient undergoing shallow breathing that were measured and derived, in accordance with some applications of the invention. The upper panel of each of the sets of graphs show the original signal, and the bottom panels show the filtered respiration related signal and heart related signal. The respiration related signal is the smoother signal with a longer cycle time compared to the heart related signal.

As described hereinabove, for some applications, the criteria that are utilized by shallow-breathing-pattern identification functionality 101 for determining that the patient is undergoing shallow respiration are as follows:

1. The heart related signal level is high and the movement profile is indicative of the fact that the patient's movements are taking place above the sensor, and/or
2. The isolated respiration signal is weak compared to the isolated heart pulse signal.

The first condition is determined by comparing the amplitude of the isolated heart pulse signal to a minimal threshold of amplitude (e.g. 5000 au). The first condition is satisfied if the extracted amplitude is higher than the threshold.

The second condition is determined by determining that a ratio between the strength of the filtered heart related signal and that of the filtered respiratory signal crosses a threshold. For example, the ratio between the strength of the filtered heart related signal to that of the filtered respiratory signal may be compared to a threshold (e.g., 0.5:1), and the second condition is satisfied if the determined ratio is higher than the threshold. Alternatively, the ratio between the strength of the filtered respiratory signal to that of the filtered heart related signal may be compared to a threshold (e.g., 2:1), and the second condition is satisfied if the determined ratio is less than the threshold.

Reference is again made to FIG. 4. For some applications, pattern analysis module 16 of system 10 includes a patient-position identification functionality 104 that is configured to identify time periods when the patient is directly above the sensor, e.g., utilizing a continuous analysis of the patient's movement patterns. This analysis includes behavior of the absolute and relative amplitude of patient movements, directionality of patient movement (e.g., movement above the signal's baseline or below the signal's baseline), and the timings of occurrences of movement. For example, for some applications, when the patient puts his weight directly on top of sensor 30, the baseline of the sensor reading goes up, and when the patient's weight moves off the sensor onto other areas of the mattress, the baseline of the sensor reading goes down. Through continuous analysis of the signal, time periods during which the patient's weight is directly on top of the sensor are identified through the increase in the baseline of the motion signal. Alternatively or additionally, pattern analysis module 16 of the system determines when the patient's weight is directly on top of the sensor by assuming that the amplitude of the motion readings when the patient's weight is on top of the sensor is higher than when the patient is not directly on top of the sensor. Alternatively or additionally, pattern analysis module 16 of the system determines when the patient's weight is directly on top of the sensor by utilizing a camera that is used by the pattern analysis module to identify the patient's position.

For some applications, pattern analysis module 16 of system 10 includes irregular-sleep detection functionality 106 configured to detect irregularities of a patient's sleeping habits, e.g., during hospitalization, nursing homes stay, or during the patient stay at his home. This indication assists a care provider in identifying the existence of an underlying medical condition or a deterioration of the patient's medical condition. For some applications, this indication is used to identify deterioration in the condition of chronic patient suffering from chronic respiratory or cardiac conditions such as congestive heart failure, chronic obstructive pulmonary disease, cystic fibrosis, and/or asthma.

The sleep irregularity level determined by the irregular-sleep detection functionality is typically based on an analysis of the patient's behavior during a period of 24 hours. Several sleep related features are extracted and a combined score of these extracted features represents the severity of the patient's sleep irregularity. Typically, these parameters are identified through analysis of mechanical signals collected from sensor 30 (which is typically a sensor placed under the patient's bed). For some applications, a night is defined as a given block of time, e.g. from 20:00 to 07:00 of the next day, and a day is defined as a given block of time, e.g. from 07:00 to 20:00.

For some applications, the system extracts one or more of the following sleep related features:

6. Number of bed exits during the night. For example, more than 3 exits may be interpreted by the system as an irregularity.
7. Number of sleeping hours during the night. For example, less than 5 hours may be interpreted by the system as an irregularity.
8. Number of sleeping hours during the day. For example, more than 3 hours may be interpreted by the system as an irregularity.
9. Number of posture changes by the patient during the night. For example, more than 12 changes may be interpreted by the system as an irregularity.
10. Number of periods with large movements during the night, For example, more than 12 periods with large movements during the night may be interpreted by the system as an irregularity. Typically, a period of several minutes (e.g., about 15 minutes) is interpreted as a period, such that multiple adjacent movements are counted as "a single period with large movements".

For some applications, system 10 alerts a care provider upon detection of a need for medical attention for patients staying at their home. This alert is generated if one or more of the following indications provide abnormal values:

7. Nightly average of heart rate (e.g., higher than 100 BPM or lower than 40 BPM).
8. Nightly average of respiration rate (e.g., higher than 30 Br/min or lower than 8 Br/min).
9. Sleep irregularity indication, e.g., as described hereinabove.
10. Fast and/or shallow respiration indication, e.g., as described hereinabove.
11. Increase in the nightly average of the heart rate as compared to one or more previous nights (e.g., a change of over 15 percent).
12. Increase in the nightly average of the respiration rate as compared to one or more previous nights (e.g., a change of over 20 percent).

Figure 10:
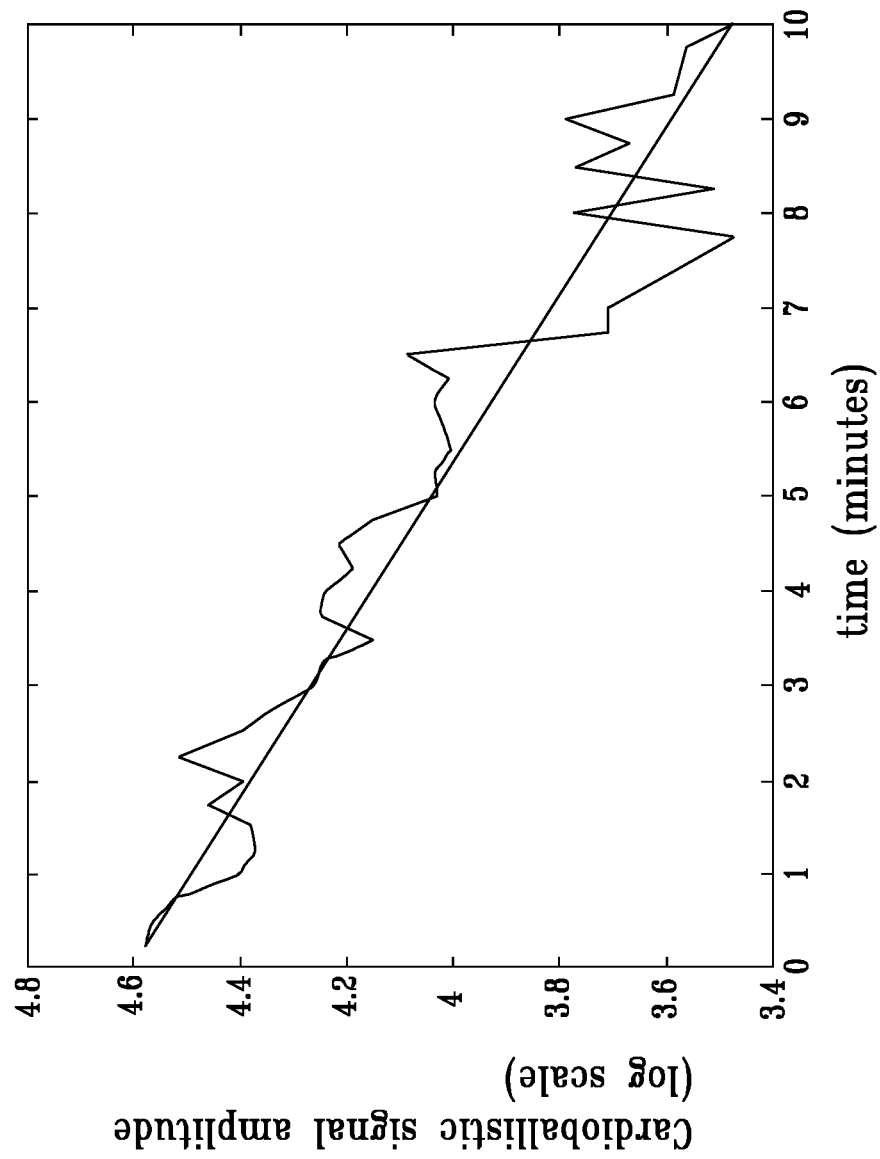
FIG. 10 is a graph showing sample results measured on a patient whose condition deteriorated, in accordance with some applications of the present invention.

Reference is now made to FIG. 10, which is a graph showing sample results measured on a patient whose condition deteriorated, in accordance with some applications of the present invention. The y-axis of the graph represents the amplitude of the patient's cardio-ballistic signal on a logarithmic scale. The straight line is the extracted trend of the cardio-ballistic amplitude measurements. It may be observed that the amplitude of the cardio-ballistic signal of the patient whose condition deteriorated underwent a decreasing trend over the course of several minutes. Therefore, in accordance with some applications of the present invention, a decrease in the amplitude of a patient's cardio-ballistic signal is used as an indication that the patient's condition is deteriorating.

For some applications, pattern analysis module 16 of control unit 14 of patient monitoring system 10 includes a decreasing-cardioballistic-amplitude-detection functionality 108, which is configured to detect a pattern of decreasing cardio-ballistic amplitude (which typically indicates weakening of the heart function and, potentially, death of the patient), and to generate an alert in response thereto. For some applications, functionality 108 is configured to calculate and store the amplitude of the patient's cardioballistic signal over each block of time having a given time period (for example, 0.5 seconds). The trend of the amplitude of the patient's cardioballistic signal in the past several minutes (for example 10 minutes) is determined by analyzing the amplitude of the heart pulse signal for the blocks of time. Functionality 108 may determine that the patient is undergoing decreasing heart pulse amplitude in response to one or more of the following indications:

A decreasing trend in the patient's heart pulse amplitude;
The decrease being substantial (for example at least 70 percent reduction in the amplitude over the time period); and/or
The duration of the decreasing trend being relatively short but not instantaneous (for example, more than 1 minute, e.g., between 3 minutes to 30 minutes).

For some applications, pattern analysis module 16 of control unit 14 of patient monitoring system 10 includes a cardiac-arrhythmia-detection functionality 110 configured to detect a pattern of heart rate measurements indicating abnormal cardiac condition that, in turn, is indicative of cardiac arrhythmia, utilizing the sensor signal of sensor 30

(which is typically a mechanical sensor placed under the mattress of a bed). Functionality 110 may determine that the patient is undergoing cardiac arrhythmia in response to one or more of the following indications:

High heart rate (for example, higher than 110 BPM); and/or

Low variability of the heart rate measurements (e.g. a standard deviation of measurements during 1 minute that is lower than 3).

An alert that is indicative of an abnormal cardiac condition is typically activated by functionality 110 if the above measurements are consistent for several minutes (for example, for more than 60 minutes). By combining the requirement for low standard deviation with the requirement for high heart rate there is typically a reduction in the number of false alerts that would otherwise be given for patients who utilize beta blockers and/or pacemakers.

For some applications, pattern analysis module 16 of control unit 14 of patient monitoring system 10 includes cardiac-risk-detection functionality 112 configured to identify situations in which utilizing a contact-free non-ECG monitor is not recommended and instead a full ECG and/or telemetry monitor is recommended to be used to monitor the patient. In response to detecting such a situation, functionality 112 generates an alert to a clinician indicating that a full ECG study is recommended, or that continuous monitoring with a telemetry system is recommended. In some applications, the alert is generated in response to identifying one or more of the following for a substantial period of time (e.g., 20 minutes to 12 hours, for example 1 hour):

4. Low detection rate of the heart rate of the patient versus a baseline, during time periods during which large body movement is not detected (e.g. detection rate of less than 60 percent when the patient is not showing large body motion but is in bed) while simultaneously having normal respiratory rate detection rates (e.g. over 70 percent) as measured versus a baseline.
5. Abnormally large range of heart rate results suggesting unstable heart rate, for example, a range of readings that is over 50 percent of a defined average, or standard deviation that is over 35 percent of a defined average, and/or an increase in standard deviation by more than 75 percent versus the average standard deviation based on the previous 24 hours.
6. Abnormal heart rate reading patterns, such as changes in a heart rate average baseline (for example, an increase in the baseline from 80 beats per minute to 120 beats per minute, where the baseline is defined as the median reading over the last 1 hour, or alternatively the median reading over the last 1 hour but only for those minutes during which patient large body motion was not detected).

A left ventricular assist device (LVAD) is a surgically implanted mechanical device that helps the heart pump blood, after a permanent damage to the left ventricle. Most machines pump blood continuously, such that it becomes difficult to detect heart rate by detecting palpation. In some applications, system 10 is used with a patient who has had implanted a continuous-flow left ventricular assist device. Heartbeat pattern analysis module 23 of pattern analysis module 16 of control unit 14 of patient monitoring system 10 is configured to analyze the sensor signal of sensor 30 and to identify the pumping of the patient's right ventricle by identifying the cardio-ballistic signal from the still functioning right ventricle. In response thereto, the heartbeat pattern analysis module calculates the patient's heart rate.

Reference is again made to FIG. 4. For some applications, the pattern analysis module includes a patient identification module 102. The patient identification module is configured to determine which motion signals detected by motion sensor 30 were generated by the patient. For example, in cases in which the patient who is being monitored is sharing a bed with a second person (e.g., the patient's partner), the patient identification module determines which components of the motion signal detected by the motion sensor were generated by the patient and which were generated by the second person. The pattern analysis module then analyzes the components of the signal that were generated by the patient, and generates outputs (such as alerts), as described herein, in response thereto. For some applications, the patient identification module is configured to determine when the patient is out of bed by determining that the motion signal detected by the motion detector is being generated by the second person. For some applications, the patient identification module is configured to determine which components of the motion signal detected by the motion sensor were generated by the patient even when the patient is smaller than the second person.

For some applications, patient identification module 102 is configured to determine which components of the motion signal detected by motion sensor 30 were generated by the patient using one or more of the following techniques:

a. The patient identification module identifies patterns (e.g., a respiratory pattern, a heart rate pattern, and/or a motion pattern) that are characteristic of, respectively, the patient and the second person. The patient identification module then determines that components of the signal that correspond to the characteristic patterns of the patient have been generated by the patient. For some applications, the patient identification module learns characteristic patterns of the patient by utilizing a weight sensor (e.g., as described hereinbelow), and/or or utilizing long term average patterns of the patient. For some applications, in response to an input to system 10, the pattern identification module operates in a learning mode, in which the module learns characteristic patterns of the patient.

b. The patient identification module identifies characteristic signal strengths generated, respectively, by the patient and by the second person. For example, the sensor may be disposed underneath the patient who lies on a first side of the bed and the second person may typically lie on the second side of the bed. In such cases, signals generated by the patient are typically characterized as being of greater strength than those generated by the second person. Alternatively, the patient may be smaller than the second person, and may therefore generate signals that are characterized as being weaker than signals generated by the second person.

Figure 11:
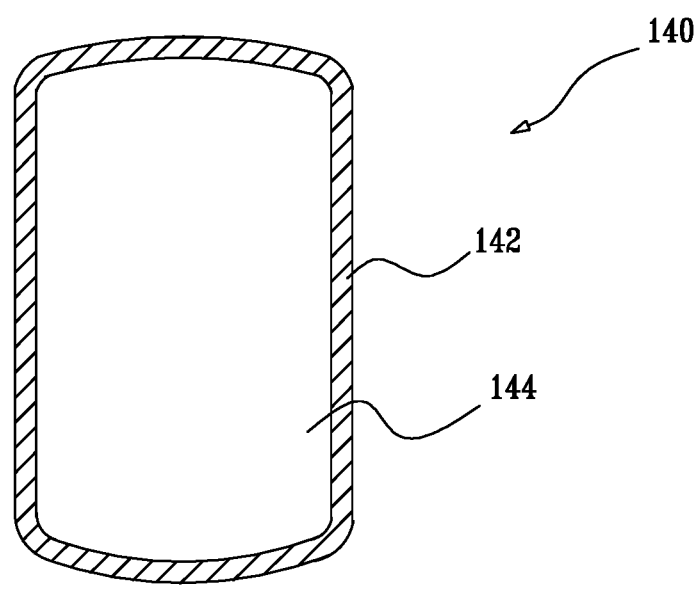
FIG. 11 is a schematic illustration of a semi-rigid sensor plate that is used as a motion sensor, in accordance with some applications of the present invention.

Reference is now made to FIG. 11, which is a schematic illustration of a semi-rigid sensor plate 140 that is used as motion sensor 30, in accordance with some applications of the present invention. For some applications, the sensor is designed and/or placed under the patient's bed such as to detect only motion of the patient who is lying on the side closer to the sensor. The sensor mechanical properties are designed to collect the vibration mechanical signal only locally from the patient lying directly on top or very close to the sensor. This allows mechanical filtering of signals coming from the partner, and detection of only the signal of the patient on top of the sensor. For some applications, edges 142 of the sensor plate are hardened with respect to a central portion 144 of the sensor plate. Typically, this prevents torque from the side of the sensor plate from bending the sensor plate, and allows only direct forces generated from on top of the sensor to affect the plate such as to generate a sensor signal. In some applications, the sensor hardening on the circumference is achieved by mechanically preventing a 2-5 mm rim of the semi-rigid sensing plate from vibrating. This typically substantially reduces the signal generated by the second person as compared to that generated by the patient.

In some applications, where monitoring and alerting requirements are not immediate, a retrospective analysis is performed by the patient identification module to remove the partner's interference on the sensor signal, by analyzing the trends and signal properties, for example, in accordance with the techniques described hereinabove. For some applications, the patient identification module uses the pulse amplitude to separate two patients after building a template for each. The signal that has the higher pulse amplitude is identified as the signal coming from the patient and the other is identified as the one coming from the partner. In some applications, the patient and the partner are differentiated by the harmonic frequency spectrum of each one's motion signal. For example, higher harmonics may indicate that the signal is coming from the patient, who is physically closer to the sensor, and the signal with lower harmonics belongs to the partner, who is further away from the sensor. Alternatively or additionally, a plurality of sensors are used in order to map the signal strength in different locations in the bed. The signal that is detected in the sensor or sensors located closer to the partner is used in order to subtract out the components relating to motion of the partner from the signal detected by the sensor under the patient.

For some applications, system 10 comprises multiple motion sensors 30 on a single support element (such as a semi-rigid plate), as well as control unit 14, and user interface (U/I) 24. Using a combination of sensors on the same semi-rigid plate allows complementary information derived from the different sensors and their different properties to be effectively integrated.

Each motion sensor may comprise a ceramic piezoelectric sensor film piezoelectric, vibration sensor, pressure sensor, accelerometer or strain sensor. Any combination of two or more of the above sensors can be used. For some applications, an effect of different sensors having different sensing characteristics is achieved by using two or more of the same type of motion sensor placed in different locations, e.g., on different substances, or at different location on the same substance.

For some applications of the current invention, the following three types of sensors are used:
4. Piezo ceramic sensor.
5. Piezo film sensor.
6. Accelerometer.

For some applications, the piezo ceramic sensor is placed on a semi-rigid plate and located on the center of the plate. It is used for detection of parameters such as heart rate, respiration rate, bed-exit detection and movement. For some applications, the piezo film sensor is attached to the same semi-rigid sensor plate, as close as possible to the center of the plate. For some applications, it is attached to the longitudinal axis of the sensor plate, and is oriented horizontally with respect to the longitudinal axis of the sensor plate. For some applications, the capacity of the implemented piezo film sensor is lower than that of the piezo ceramic sensor. Thus, the piezo film sensor is typically more sensitive than the piezo ceramic sensor for tracking fast changes such as single heartbeat, and beat-by-beat identification. In different patient positions and patient conditions the relative quality of the signals detected by the piezo ceramic sensor and piezo film sensor may vary. For some applications, pattern analysis module 16 of control unit 14 (e.g., signal analysis functionality 90 of the pattern analysis module) calculates a quality index for the readings from each of the sensors and continuously selects the results with the higher quality index. Additionally, in some situations, one of the sensors may more effectively detect patient motion readings. The motion readings may be used to filter out false readings from both sensors.

For some applications, an accelerometer is attached to the same semi-rigid plate. The accelerometer signal is, in some cases, a better indicator of patient motion or bed exit than the piezo technology sensors. As described above, for some applications, a processing circuit of control unit 14 continuously selects the highest quality sensor signal. For some applications, selection of the highest quality sensor signal facilitates effective, rapid detection of patient bed exit by the system. In addition, for some applications, utilizing the accelerometer, control unit 14 of system 10 detects and alerts whenever the sensor is placed upside down. Alternatively or additionally, control unit 14 of system 10 utilizes the accelerometer in order to detect whenever the sensor is hung from a special hook on the user interface module and shifts the system state into a pause state until the sensor is placed again in the bed.

In accordance with the above, for some applications, control unit 14 is generally configured to identify one of a plurality of sensors as having a higher signal quality than at least a second one of the plurality of sensors, and in response thereto, to assign greater weight to data that were detected by the first sensor than to data that were detected by the second sensor.

Reference is now made to FIGS. 12A-B, which are schematic illustrations of motion sensor 30 coupled to a chair 150, in accordance with some applications of the present invention. FIG. 12A shows the sensor on the chair when the patient is not sitting on the chair. FIG. 12B shows the sensor on the chair when the patient is sitting in the chair. For some applications, system 10 performs all or some of the clinical measurements and analysis described herein with a mechanical sensor placed in a chair instead of in a bed. For some applications, sensor 30 includes a semi-rigid sensor plate that is placed in a pillow on which the patient sits or rests his back. For some applications, in addition to performing clinical measurements, system 10 detects when a patient exits the chair and alerts a clinician in order to prevent a potential fall by the patient.

For some applications, in order to facilitate detection of the patient leaving the resting surface under which there is a sensor (e.g. exiting the bed or getting off from a chair), a mechanical element 152 is attached to the sensor. When there is no patient above the sensor plate (FIG. 12A), the element sets the sensor into an initial state in which the sensor is operative but is configured to indicate that the patient is not on the sensor. The sensor is configured such that weight of any patient sitting or lying above the sensor will move the sensor from its initial state to a different state, as shown in FIG. 12B.

Typically, as shown, the mechanical element causes the sensor to assume a given orientation when the patient is not positioned above the plate. When the patient is positioned above the sensor, this causes the sensor to move from the given orientation. The movement of the sensor from the given orientation is interpreted by the system as indicating that the patient is positioned above the sensor. For example, as shown, for some applications of the current invention, the mechanical element is a rod attached to the underside of the plate of the sensor in parallel to the horizontal axis, but not exactly on the axis, such that the plate pivots about the rod. This breaks the symmetry of the plate and causes inclination of the sensor when there is no patient above the plate, thereby causing the sensor to be in the initial state of the sensor. When a patient is lying on the mattress or sitting on a chair with a sensor plate below, the weight of the patient moves the sensor's orientation from its initial state to a different state. For some applications, an accelerometer is used to effectively differentiate between the two states.

For some applications, based on a signal from sensor 30, sensor 30 being as shown in FIGS. 12A-B, control unit 14 detects if the patient who is sitting above the plate is leaning forward, as opposed to leaning to the sides. The rod is used to enhance the effect of movements in the backward-forward direction, while attenuating movements in other directions.

For some applications, system 10 has one sensor plate in a hospital bed and one sensor in a chair next to the bed. When the patient is moved from the bed to the chair as is often done with hospitalized patients, system 10 automatically or manually changes to monitoring the patient in the chair, and vice versa. For some applications, system 10 logs and displays statistical information on one or more patients' utilization of beds and chairs. This is useful, for example, for verifying that post surgical patients are moved quickly enough and frequently enough to a chair which is generally considered conducive to their healing process. For some applications, the control unit is configured to generate an alert in response to detecting that the patient has not moved from the bed to the chair for a period of time that is greater than a given threshold. For some applications, the control unit determines whether the patient moved from the bed to the chair within a given time period after the generation of the alert and generates a log in response thereto. Typically, if, within a given time period after the generation of the alert the patient has not been moved from the bed to the chair, the control unit generates a reminder to move the patient. For some applications, the control unit is configured to determine that the patient is likely to be sleeping, and is configured to withhold generating the alert in response thereto, for example, in accordance with the techniques described hereinabove.

A big challenge in modern healthcare is patient behavioral compliance. In many cases it is challenging to get people to behave in the best interest of their own health. Some estimates show that over 50 percent of healthcare costs are behavioral related. For example, it is challenging to get chronic patients to take their prescribed medication, apnea patients to use their continuous positive airway pressure (CPAP) devices, etc. In accordance with some applications of the present invention, in order to facilitate patient compliance, at least one physiological parameter of a patient is continuously monitored, and the patient is warned when changes in the at least one parameter occur that are likely to be correlated to lack of compliance of the patient. This provides an important feedback mechanism that clarifies to the patient the importance of complying with the medication or other care protocol in order to improve compliance of the patient. Typically, system 10 is configured to effect a feedback loop that is as immediate as possible and the system is configured to generate an output to the patient that indicates to the patient the possible impact of failure to follow the care protocol. Further typically, the system is configured to effect the feedback loop in a way that requires no or minimal compliance by the patient.

For some applications, system 10 utilizes non-contact sensor 30, which is typically a sensor under the mattress or within a chair or cushion to continuously monitor the patient's respiratory, cardiac, and motion parameters automatically (e.g., in accordance with techniques described herein). The system is preset with the type of changes in parameters that may indicate that a patient is not compliant with protocol. In some applications, the system is used with asthma patients who are prescribed daily medication. If a level of respiratory rate, restlessness in sleep, use of auxiliary muscles and/or increase in coughing rate is detected that is higher than historic baseline or above a threshold, then an alert is generated to the patient that indicates to the patient that the patient's condition has deteriorated in a manner that may be associated with non-compliance with a protocol by the patient. For example, the system may generate a preset message (e.g., an audio message or a textual message) such as "significant change in a respiratory parameter detected, please verify that you have taken the prescribed medication." For some applications, the message includes an indication of the protocol that the patient should follow, e.g., the actual medication and dosage as prescribed by a clinician and entered into the system.

For some applications, pattern analysis module 16 of control unit 14 of patient monitoring system 10 includes protocol-input functionality 114 that is configured to receive an input that is indicative of a treatment protocol that has been assigned to the patient. The pattern analysis module (e.g., signal analysis functionality 90 of the pattern analysis module) is configured to analyze the physiological parameter and the inputted treatment protocol and, in response thereto, to determine that the patient has failed to follow the treatment protocol. The system further includes user interface 24 configured to generate an output (e.g., an audio output, or a textual output) that is indicative of a correlation between the physiological parameter and non-compliance by the patient with the treatment protocol.

For some applications, the system shares the information with a care provider (e.g., a family member or a clinician), and/or the system generates a compliance report in response to a request from the care provider, and/or at given time intervals, e.g., on a weekly or monthly basis. Typically, the system is configured to share the information regarding the patient's compliance with protocol only with specific individuals (e.g., a care provider that the patient has identified). Typically, sharing the information with only specific individuals increases the willingness of patient to use the system, since this reduces privacy concerns and loss of insurance privilege concerns that the patient might otherwise have. For some applications, the control unit 14 and/or user interface module 24 of system 10 are implemented in a mobile device (such as a cellular phone, or a tablet computer).

For some applications, system 10 provides general alerts about changes in a patient's condition (e.g., as described hereinabove, and/or as described in US 2011/0112442 to Meger and in US 2012/0253142 to Meger, both of which applications are incorporated herein by reference), in addition to alerts that may be related to compliance of the patient with a protocol, such as a protocol of prescribed medication. For example, the above described system for monitoring compliance of a patient with asthma medication may also monitor the patient's heart readings on a continuous basis, while the patient is in bed. The system may be configured to generate an alert in response to detecting parameters that are indicative of an approaching episode, or a currently occurring episode of cardiac arrhythmia or cardiac distress. This is intended to enhance the value of the system in the mind of the patient and enhance the chances that the system will be used continuously.

For some applications, system 10 is used to monitor compliance of the patient with a protocol of use of a continuous positive airway pressure (CPAP) device, and/or a similar device, that is used to prevent sleep apnea. The system is typically configured to remind patients to use the device if the number of apneas detected increases versus a baseline. Sleep apnea is known to affect cardiac function. Therefore, for some applications, system 10 is used to encourage a patient to use a CPAP device, or a similar device, by showing the patient the changes in cardiac condition that take place when the CPAP device is not used and how that increases the patient's risk of undergoing a severe cardiac deterioration.

For some applications, the system is used to monitor a patient who is taking medication to control cardiac function. In response to detecting a change in the patient's cardiac rate pattern, the system generates an alert (e.g., an audio alert, or a textual alert) to the patient that indicates to the patient that the patient's condition has deteriorated in a manner that may be associated with non-compliance with the medication protocol.

For some applications, system 10 is configured to generate an output that indicative of a correlation between an improvement in the patient's condition and compliance of the patient with a protocol. In this manner, the system provides positive reinforcement to following care protocols. For example, the signal analysis functionality may determine that the patient has followed the treatment protocol by identifying an improvement in a physiological parameter of the patient, and, in response thereto, the user interface may be configured to generate an output that is indicative of a correlation between the improvement in the physiological parameter and compliance by the patient with the treatment protocol. For example, if a patient starts using a new asthma medication and the system then determines that the patient's respiratory rate, cough rate, restlessness in sleep, and/or use of auxiliary muscles have decreased with respect to a baseline, the system may generate an output (e.g., an audio output, or a textual output) that indicates a relationship between an improvement in the patient's condition, and compliance by the patient with the protocol. For example, system 10 may provide the patient with a message (e.g., an audio message, or a textual message) such as "your use of the medication has resulted in a 10 percent reduction in coughs, 20 percent reduction in restlessness in sleep, and 5 percent reduction in the respiratory rate."

For some applications, the signal analysis functionality may determine that the patient has not followed the treatment protocol by identifying that there has not been an improvement in a physiological parameter of the patient, or in response to determining that there has been a deterioration in a physiological parameter of the patient. In response thereto, the user interface may generate an output that is indicative of a correlation between the lack of improvement in the physiological parameter, or the deterioration in the physiological parameter, and compliance by the patient with the treatment protocol. For some applications, system 10 has access to an internal or external database with information about the risk impact of changes in vital signs and shares relevant facts with the patient in order to convince the patient to take the medication. For example, system 10 may generate a message (e.g., an audio message, or a textual message) indicating a correlation between a change in a physiological parameter and a risk of undergoing a clinical episode. For example, system 10 may generate a message (e.g., an audio message, or a textual message) to the patient such as "The lack of use of the medication has resulted in a 20 percent increase in heart rate in sleep. Clinical trials have shown that such an increased heart rate in sleep is associated with a 50 percent increase in the prevalence of heart attacks".

Various manufacturers provide solutions that measure adherence of a patient to a medication-administration protocol. Such devices are commonly called electronic medication monitoring (EMM) devices. Despite the use of such devices, patients often do not take their prescribed medication. For some applications, system 10 communicates with the EMM device. Upon detection that a medication was not used, system 10 (e.g., signal analysis functionality 90 of pattern analysis module 16) collects information about changes in at least one physiological parameter of the patient and generates an output (e.g., an audio message, or a textual message) to the patient that is indicative of a correlation between a change in the physiological parameter, and non-compliance of the patient with a protocol. For example, in the case of an asthmatic patient, such as in the example described hereinabove, the system may generate a message (e.g., an audio message, or a textual message) such as "Because you have not taken your medication, your respiratory rate increased by 10 percent and your quality of sleep score was reduced by 10 percent". Alternatively, an output may be generated that is indicative of a correlation between adherence by the patient to the medication-administration protocol and the change in the at least one the physiological parameter, the output being generated in response to receiving an indication from the medication monitoring device that the patient has adhered to the medication-administration protocol.

It is noted that, in the context of the present application, the terms "compliance" and "adherence" are used interchangeably with respect to a treatment protocol and/or a medication-administration protocol.

For some applications, system 10 calculates a quality of sleep index based on the measured respiratory, cardiac and motion parameters. System 10 then identifies changes in quality of sleep and correlates that with the lack of compliance of the patient with the therapy. In response to detecting deterioration in the patient's quality of sleep, the system generates an alert (e.g., an audio alert, or a textual alert) to the patient that indicates to the patient that the patient's quality of sleep has deteriorated in a manner that may be associated with non-compliance with a protocol. For example, the system may generate a message (e.g., an audio message, or a textual message) to the patient such as "please verify that you have taken the medication, possible non use of the medication has resulted in a 10 percent decline in your quality of sleep score."

For some applications, pattern analysis module 16 includes athletic-exercise-indication-receiving functionality 116, which is configured to receive an indication of a level of athletic exercise performed by the patient. Alternatively or additionally, pattern analysis module 16 includes nutrition-indication-receiving functionality 116, which is configured to receive an indication of a nutritional intake of the patient. The pattern analysis module calculates a quality of sleep index and correlates that with the data regarding the level of athletic exercise performed by the patient, and/or the data regarding the patient's nutritional intake. For example, system 10 may interface with a fitness watch such as that manufactured by Polar Electro Inc. of Lake Success, N.Y. This allows the patient to become aware of the cross effects of exercise and sleep. For example, if the exercise results are improved after a good night sleep this information is highlighted to the user in order to further motivate him to take the necessary steps to get better sleep. Similarly, if better sleep is achieved after an exercise session is performed this further motivates additional exercise activity. Similar information is collected and presented in some applications as regarding the correlation of diet and sleep. For some applications, the athletic-exercise-receiving functionality receives the indication of the level of athletic exercise performed by the patient by manually receiving an input that is indicative of the level of athletic exercise performed by the patient. Alternatively, the athletic-exercise-receiving functionality may interface with another system, as described above. Similarly, for some applications, the nutrition-receiving functionality is configured to receive the indication of the patient's nutritional intake by manually receiving an input that is indicative of the patient's nutritional intake. Alternatively, the nutrition-receiving functionality may interface with another system, as described above with respect to the athletic-exercise-receiving functionality.

In general, control unit 14 may be embodied as a single control unit 14, or a cooperatively networked or clustered set of control units. Control unit 14 is typically a programmed digital computing device comprising a central processing unit (CPU), random access memory (RAM), non-volatile secondary storage, such as a hard drive or CD ROM drive, network interfaces, and/or peripheral devices. Program code, including software programs, and data are loaded into the RAM for execution and processing by the CPU and results are generated for display, output, transmittal, or storage, as is known in the art. Typically, control unit 14 is connected to one or more sensors via one or more wired or wireless connections. Control unit 14 is typically configured to receive signals (e.g., motions signals) from the one or more sensors, and to process these signals as described herein. In the context of the claims and specification of the present application, the term "motion signal" is used to denote any signal that is generated by a sensor, upon the sensor sensing motion. Such motion may include, for example, respiratory motion, cardiac motion, or other body motion, e.g., large body-movement. Similarly, the term "motion sensor" is used to denote any sensor that senses motion, including the types of motion delineated above.

Techniques described herein may be practiced in combination with techniques described in one or more of the following patents and patent applications, which are incorporated herein by reference. In some applications, techniques and apparatus described in one or more of the following applications are combined with techniques and apparatus described herein:

U.S. patent application Ser. No. 11/048,100, filed Jan. 31, 2005, which issued as U.S. Pat. No. 7,077,810;
  U.S. patent application Ser. No. 11/197,786, filed Aug. 3, 2005, which issued as U.S. Pat. No. 7,314,451;
  U.S. patent application Ser. No. 11/446,281, filed Jun. 2, 2006, which issued as U.S. Pat. No. 8,376,954;
  U.S. patent application Ser. No. 11/552,872, filed Oct. 25, 2006, now abandoned, which published as US 2007/0118054;
  U.S. patent application Ser. No. 11/755,066, filed May 30, 2007, now abandoned, which published as US 2008/0114260;
  U.S. patent application Ser. No. 11/782,750, filed Jul. 25, 2007, which issued as U.S. Pat. No. 8,403,865;
  U.S. patent application Ser. No. 12/113,680, filed May 1, 2008, which published as US 2008/0275349;
  U.S. patent application Ser. No. 12/842,634, filed Jul. 23, 2010, which issued as U.S. Pat. No. 8,517,953;
  U.S. patent application Ser. No. 12/938,421, filed Nov. 3, 2010, which issued as U.S. Pat. No. 8,585,607;
  U.S. patent application Ser. No. 12/991,749, filed Nov. 9, 2010, which issued as U.S. Pat. No. 8,821,418;
  U.S. patent application Ser. No. 13/107,772, filed May 13, 2011, which issued as U.S. Pat. No. 8,491,492;
  U.S. patent application Ser. No. 13/305,618, filed Nov. 28, 2011, which published as US 2012/0132211;
  U.S. patent application Ser. No. 13/389,200, filed Jun. 13, 2012, now abandoned, which published as US 2012/0253142;
  U.S. patent application Ser. No. 13/750,957, filed Jan. 25, 2013, which issued as U.S. Pat. No. 8,603,010
  U.S. patent application Ser. No. 13/750,962, filed Jan. 25, 2013, which issued as U.S. Pat. No. 8,679,034;
  U.S. patent application Ser. No. 13/863,293, filed Mar. 15, 2013, now abandoned, which published as US 2013/0245502;
  U.S. patent application Ser. No. 13/906,325, filed May 30, 2013, which issued as U.S. Pat. No. 8,882,684;
  U.S. patent application Ser. No. 13/921,915, filed Jun. 19, 2013, which issued as U.S. Pat. No. 8,679,030;
  U.S. patent application Ser. No. 14/019,371, filed Sep. 5, 2013, which published as US 2014/0005502;
  U.S. patent application Ser. No. 14/020,574, filed Sep. 6, 2013, which issued as U.S. Pat. No. 8,731,646;
  U.S. patent application Ser. No. 14/054,280, filed Oct. 15, 2013, which issued as U.S. Pat. No. 8,734,360;
  U.S. patent application Ser. No. 14/150,115, filed Jan. 8, 2014, which issued as U.S. Pat. No. 8,840,564;
  U.S. patent application Ser. No. 14/231,855, filed Apr. 1, 2014, which published as US 2014/0207204;
  International Patent Application PCT/IL2005/000113, which published as WO 2005/074361;
  International Patent Application PCT/IL2006/000727, which published as WO 2006/137067;
  International Patent Application PCT/IB2006/002998, which published as WO 2007/052108;
  International Patent Application PCT/IL2008/000601, which published as WO 2008/135985;
  International Patent Application PCT/IL2009/000473, which published as WO 2009/138976;
  International Patent Application PCT/IL2011/050045, which published as WO 2012/077113;
  International Patent Application PCT/IL2013/050283, which published as WO 2013/150523; and
  International Patent Application PCT/IL2014/050644, which published as WO 2015/008285.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a plurality of patients, the apparatus comprising:
   (A) a plurality of sensors configured to detect physiological parameters of respective patients, and to generate respective sensor signals in response thereto;
   (B) at least one output unit configured to generate an output to clinicians who are caring for the patients, in response to the sensor signals;

(C) a monitoring system configured to:
   analyze clinician performance in responding to the output of the at least one output unit; and
   generate an indication of a performance level of the clinicians in response to the analyzing of the clinician performance;
   wherein the at least one output unit is configured to generate alerts in response to the sensor signals, and wherein the monitoring system is configured to analyze clinician performance by analyzing a response time of the clinicians to the generated alerts; and
(D) a location-sensing system configured to identify respective locations of a plurality of the clinicians, and to generate a location-sensing-system signal in response thereto,
   wherein the monitoring system is configured to:
      receive the location-sensing system signal,
      determine that at least one of the clinicians has responded to the alert by analyzing the location-sensing system signal, and
      analyze clinician performance in response thereto.

2. The apparatus according to claim 1, wherein the monitoring system is further configured to receive the sensor signals.

3. The apparatus according to claim 1, wherein the apparatus is for use with a plurality of resting surfaces, respective patients of the plurality of patients resting on respective resting surfaces of the plurality of resting surfaces, and wherein respective sensors of the plurality of sensors are configured to be coupled to respective resting surfaces of the plurality of resting surfaces.

4. The apparatus according to claim 1, wherein the monitoring system is configured to measure the performance level of the clinicians by analyzing a number of alerts generated over a given period of time.

5. The apparatus according to claim 1, wherein the monitoring system is configured to generate the indication of the performance level of the clinicians by measuring the performance level of the clinicians with respect to a standard performance level.

6. The apparatus according to claim 5, wherein the monitoring system is configured to measure the performance level of the clinicians with respect to the standard performance level, by measuring the performance level of the clinicians with respect to an average historic performance level over a given time period.

7. The apparatus according to claim 5, wherein the monitoring system is configured to communicate with at least one similar monitoring system that is configured to perform monitoring at at least one peer site, and wherein the monitoring system is configured to measure the performance level of the clinicians with respect to the standard performance level, by measuring the performance level of the clinicians with respect to a performance level of clinicians at the at least one peer site, the performance level of the clinicians at the at least one peer site being determined by the at least one similar monitoring system.

8. The apparatus according to claim 1, wherein the monitoring system is configured to receive an input from a clinician who is responding to an alert that is indicative of the clinician having responded to the alert, and to analyze clinician performance in response thereto.

9. The apparatus according to claim 1, wherein the monitoring system is configured to:
   analyze the sensor signals,
   determine that a clinician has responded to an alert by determining that there has been a change in one of the sensor signals that is indicative of a clinician having responded to the alert, and
   analyze clinician performance in response thereto.

10. Apparatus for use with a plurality of patients, the apparatus comprising:
   a plurality of sensors configured to detect physiological parameters of respective patients, and to generate respective sensor signals in response thereto;
   at least one output unit configured to generate alerts in response to the plurality of sensor signals; and
   a monitoring system configured to:
      analyze a rate at which the alerts are generated,
      in response thereto, determine that a setting of the at least one output unit should be changed, and
      in response thereto:
         generate an output that is indicative of a recommended change to the setting of the at least one output unit, or
         automatically change the setting of the at least one output unit.

11. The apparatus according to claim 10, wherein the apparatus is for use with a plurality of resting surfaces, respective patients of the plurality of patients resting on respective resting surfaces of the plurality of resting surfaces, and wherein respective sensors of the plurality of sensors are configured to be coupled to respective resting surfaces of the plurality of resting surfaces.

12. The apparatus according to claim 10, wherein the monitoring system is configured to generate an output that is indicative of the recommended change to the setting of the at least one output unit in response to determining that a setting of the at least one output unit should be changed.

13. The apparatus according to claim 10, wherein the monitoring system is configured to automatically change the setting of the at least one output unit in response to determining that a setting of the at least one output unit should be changed.

14. The apparatus according to claim 10, wherein the monitoring system is configured to determine that the setting of the at least one output unit should be changed by determining that a threshold used by the at least one output unit should be changed.

15. The apparatus according to claim 10, wherein the monitoring system is configured to determine that the setting of the at least one output unit should be changed in a manner that will lower the rate at which the alerts are generated, in response to the rate at which the alerts are generated exceeding a threshold rate.

16. The apparatus according to claim 10, wherein the monitoring system is configured to determine that the setting of the at least one output unit should be changed in a manner that will increase the rate at which the alerts are generated, in response to the rate at which the alerts are generated being below a threshold rate.

17. The apparatus according to claim 10, wherein the monitoring system is configured to determine that the setting of the at least one output unit should be changed by determining that a general setting of the at least one output unit should be changed in a manner that affects a response of the at least one output unit to each one of the plurality of sensor signals.

18. The apparatus according to claim 17, wherein the monitoring system is configured to determine that the general setting of the at least one output unit should be changed, in response to determining an overall alert rate at which alerts are generated based on the sensor signals from all of the plurality of sensors.

19. The apparatus according to claim 10, wherein the monitoring system is configured to automatically change alert settings of each of the plurality of sensors based on time of day.

20. The apparatus according to claim 19, wherein the apparatus is for use with a plurality of resting surfaces, respective patients of the plurality of patients resting on respective resting surfaces of the plurality of resting surfaces, and wherein respective sensors of the plurality of sensors are configured to be coupled to respective resting surfaces of the plurality of resting surfaces.

* * * * *